United States Patent [19]

Duffy

[11] Patent Number: 4,815,474
[45] Date of Patent: Mar. 28, 1989

[54] TEMPORAL TRAJECTORY ANALYSIS IN BRAIN ELECTRICAL ACTIVITY MAPPING

[75] Inventor: Frank H. Duffy, Brighton, Mass.

[73] Assignee: The Children's Medical Center Corporation, Boston, Mass.

[21] Appl. No.: 37,981

[22] Filed: Apr. 13, 1987

[51] Int. Cl.[4] ............................................. A61B 5/04
[52] U.S. Cl. ................................................... 128/731
[58] Field of Search ............................... 128/731–732; 364/417; 346/33 ME

[56] References Cited

U.S. PATENT DOCUMENTS

| 4,254,779 | 3/1981 | Miyata et al. | 364/717 X |
| 4,279,258 | 7/1981 | John | 128/731 |
| 4,421,122 | 12/1983 | Duffy | 128/731 |
| 4,579,125 | 4/1986 | Strobl et al. | 128/731 |

FOREIGN PATENT DOCUMENTS

83/03745  11/1983  PCT Int'l Appl. ................. 128/731

OTHER PUBLICATIONS

Duffy et al., "Tumor Detection from Topographic Maps of Long Latentcy Evoked Potentials: Spatial Trajectory Analysis and Cross Correlational Analyses", unpublished paper.

Duffy et al., "Brain Electrical Activity Mapping (BEAM): A Method for Extending the Clinical Utility of EEG and Evoked Potential Data", Ann. Neurol., 5:309–321 (1979).

Duffy et al., "Significance Probability Mapping: An Aid in the Topographic Analysis of Brain Electrical Activity", Electroencephalography and Clinical Neurophysiology, 51:455–462 (1981).

Duffy et al., "Topographical Display of Evoked Potentials: Clinical Applications of Brain Electrical Activity Mapping (BEAM)", Anals New York Academy of Sciences, 388:183–196 (1982).

Primary Examiner—Francis J. Jaworski

[57] ABSTRACT

Pathological changes in brain electrical activity over time caused by for example growth of a lesion are detected by producing a brain electrical activity map such as a statistical probability map, and then selecting a template or mask surrounding a suspect area, summating values of the map within the template area to form an aggregate statistical feature, and then plotting the feature over a period of time, e.g. several weeks, to form a trend plot characteristic of brain electrical activity changes.

19 Claims, 22 Drawing Sheets

FIG 2
SUBJECT FL
TREND ANALYSIS OF
FEATURES DEVELOPED BY
COMPARISON OF INITIAL
STUDIES TO
CONTROL GROUP
T-SPM
FEOD →
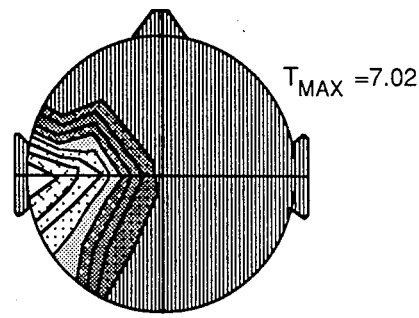
$T_{MAX} = 7.02$
TEMPLATES
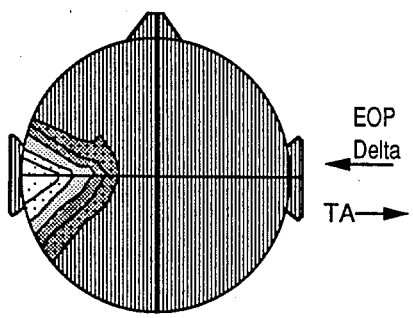
← EOP Delta
TA →
TREND PLOTS
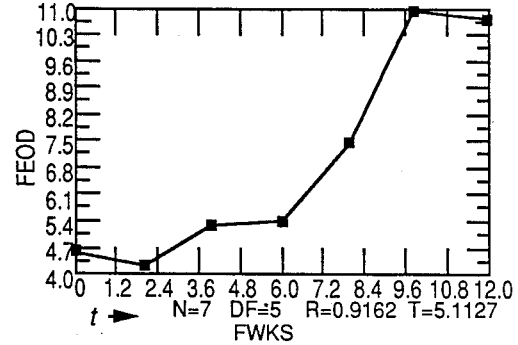
N=7  DF=5  R=0.9162  T=5.1127
FWKS
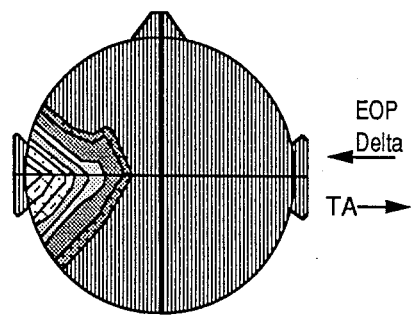
← EOP Delta
TA →
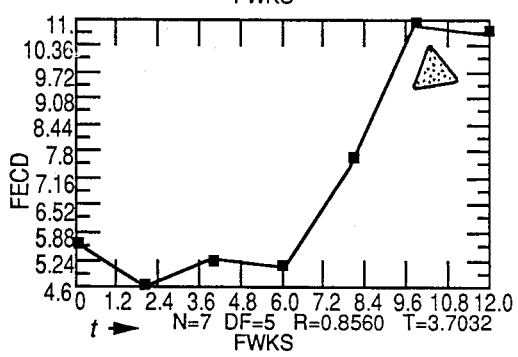
N=7  DF=5  R=0.8560  T=3.7032
FWKS
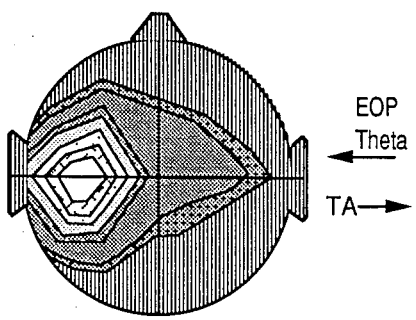
← EOP Theta
TA →
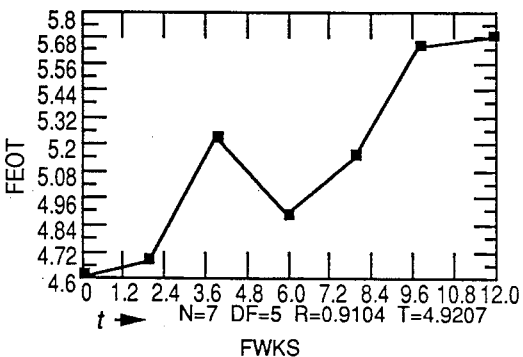
N=7  DF=5  R=0.9104  T=4.9207
FWKS
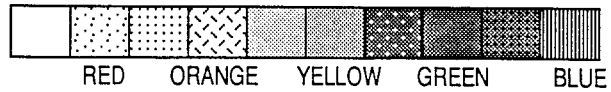
RED   ORANGE   YELLOW   GREEN   BLUE

FIG 3
PATIENT FL
TREND ANALYSIS OF FEATURES DEVELOPED BY COMPARISON
OF INITIAL STUDIES TO CONTROL GROUP- CONTINUED
TEMPLATES                TREND PLOTS
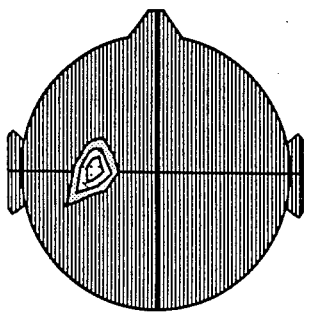 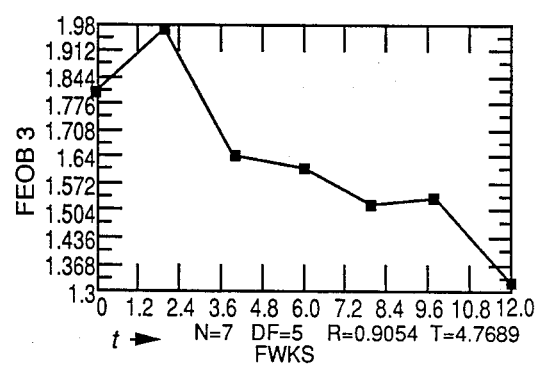
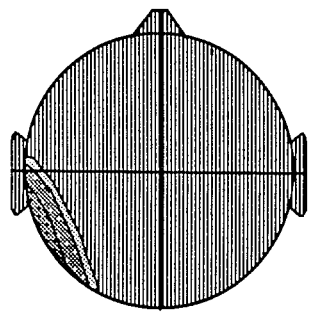 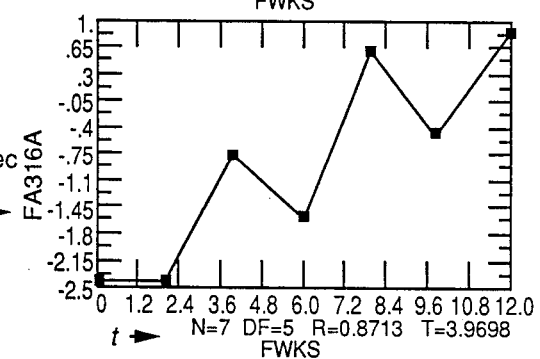
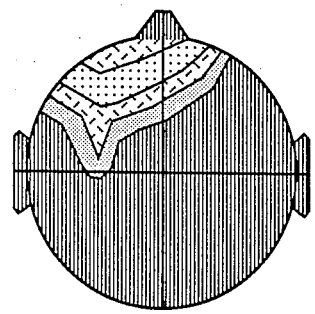 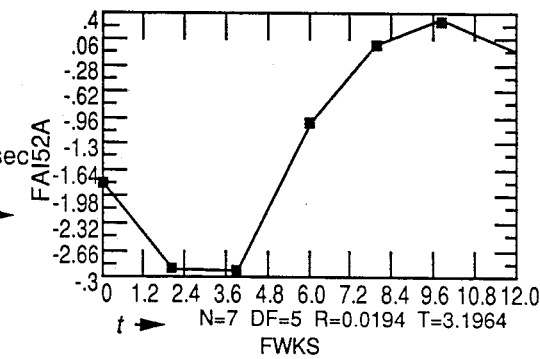
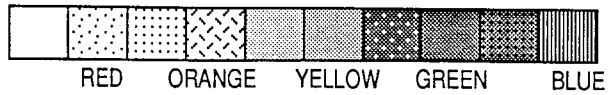

SUBJECT FL
TREND ANALYSIS OF FEATURE DEVELOPED FROM APRIORI TEMPLATES EACH MORE PROGRESSIVELY DISTANT FROM THE LEFT TEMPORAL GLIOBLASTOMA AT RISK FOR RECURRENCE

FIG 5
SUBJECT FL
APRIORI TEMPLATE FEATURE TREND ANALYSIS
(SEE PRECEDING PAGE)
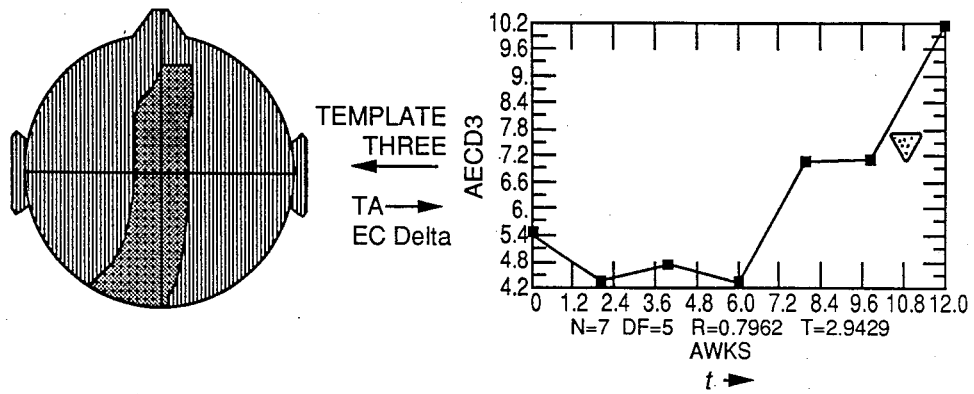
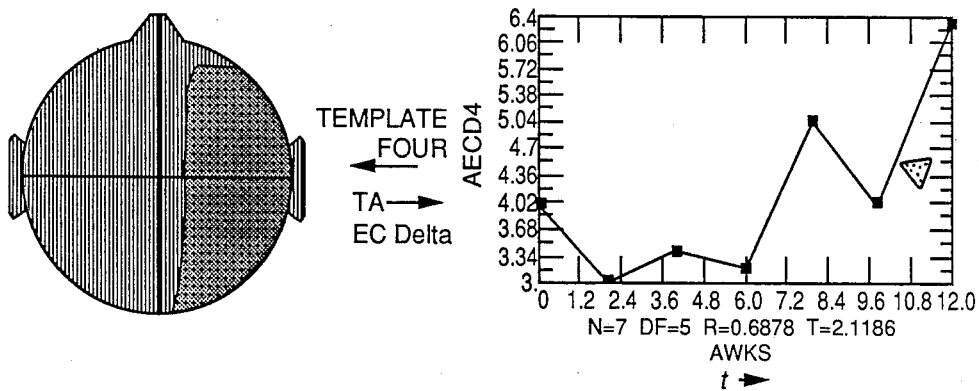
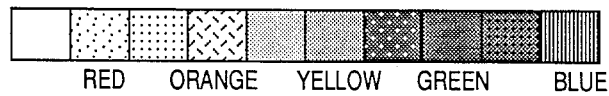

SUBJECT FL
APRIORI TEMPLATE FEATURE TREND ANALYSIS
FOR EO THETA AND AER 316

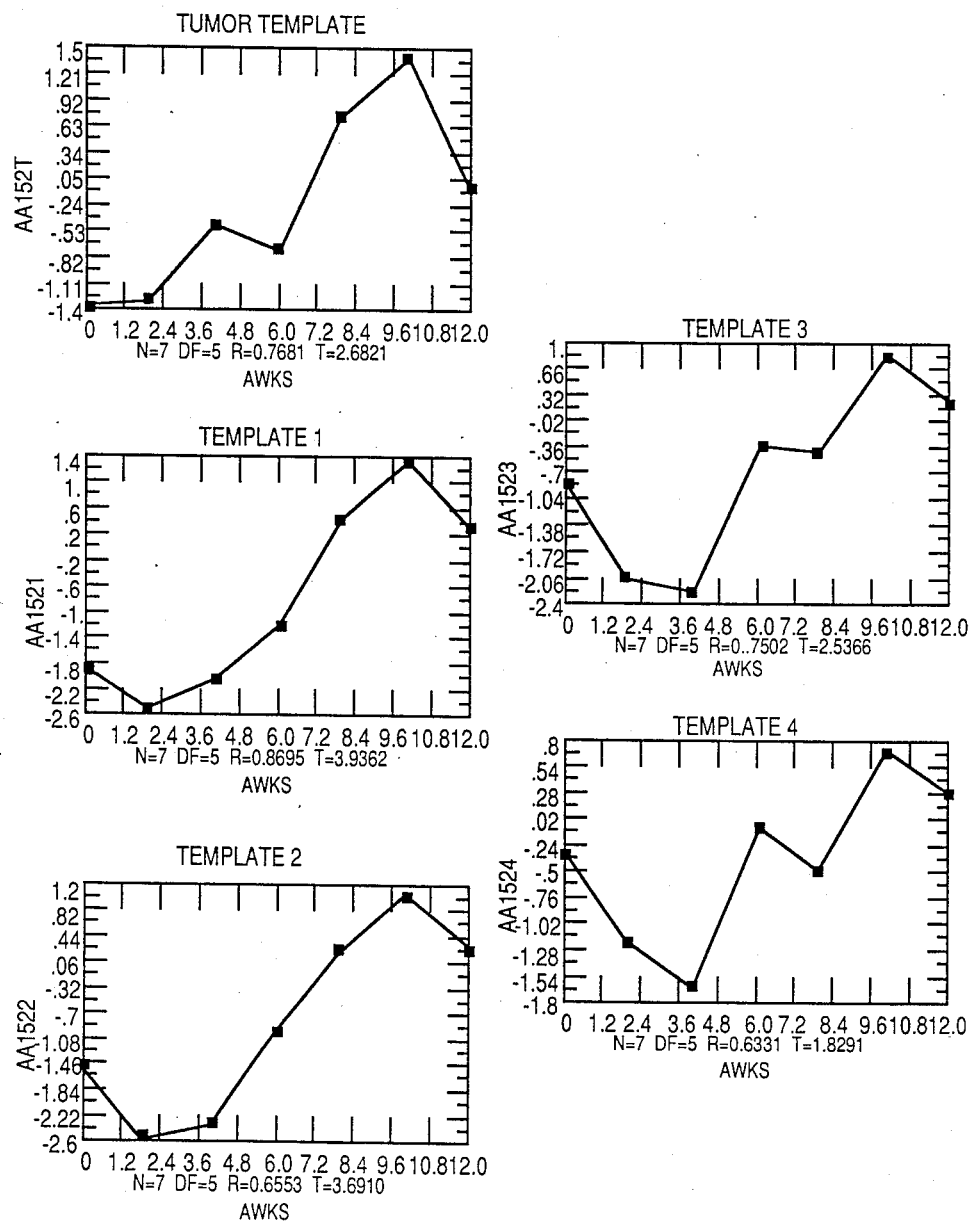
FIG 7 — SUBJECT FL, APRIORI TREND ANALYSIS FOR FEATURE AER 152

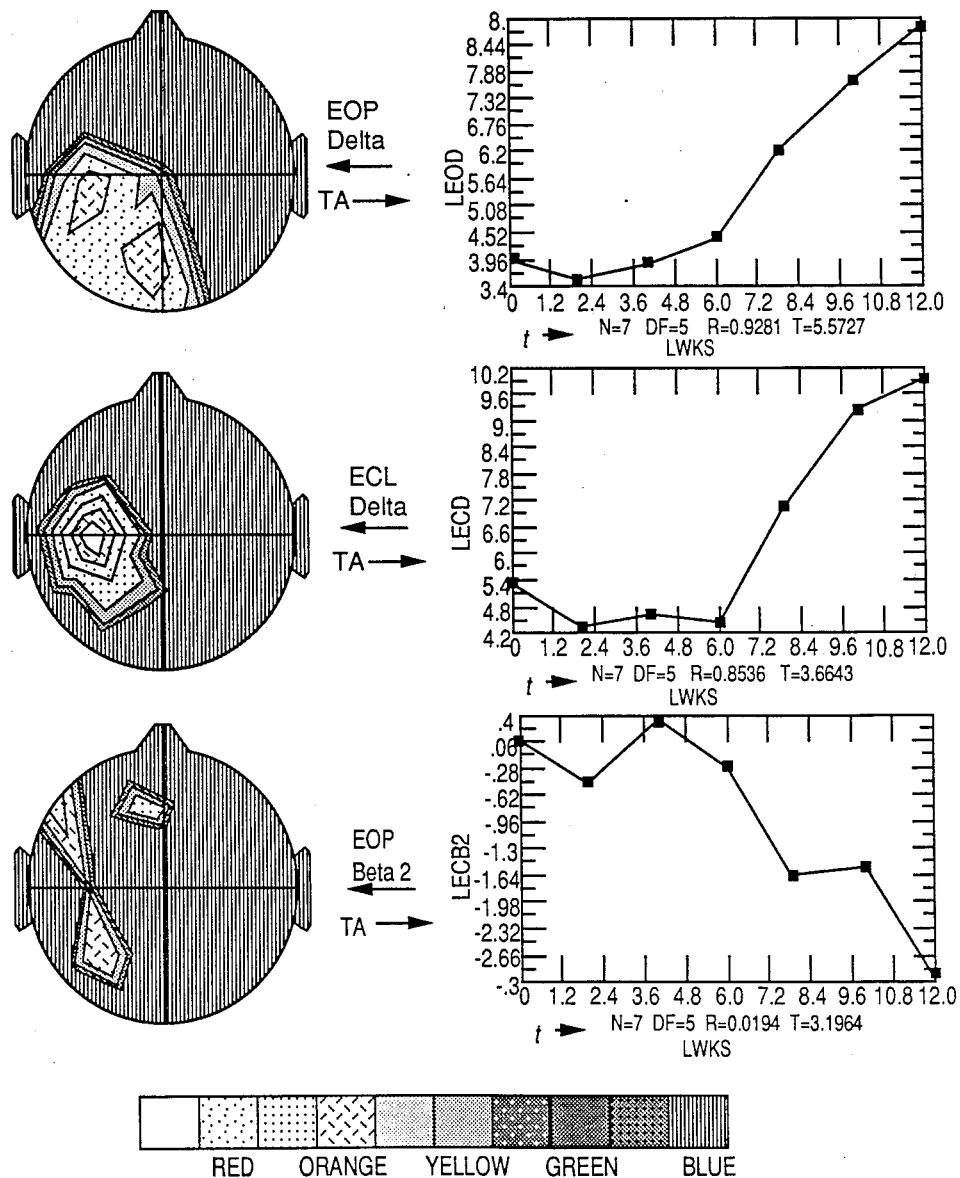
FIG 8 — SUBJECT FL
TREND ANALYSIS OF FEATURES DEVELOPED RETROSPECTIVELY BY COMPARISON BETWEEN THE FIRST AND LAST STUDIES SUBJECT FL
FIG 9   TREND ANALYSIS OF FEATURE DEVELOPED RETROSPECTIVELY BY COMPARISON BETWEEN THE FIRST AND LAST STUDIES-CONTINUED
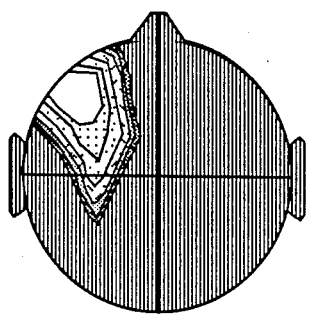
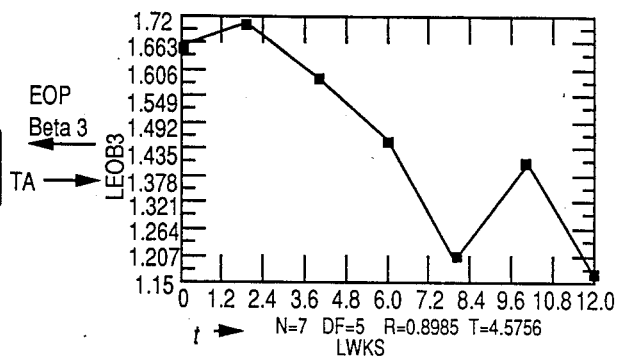
EOP Beta 3
TA →
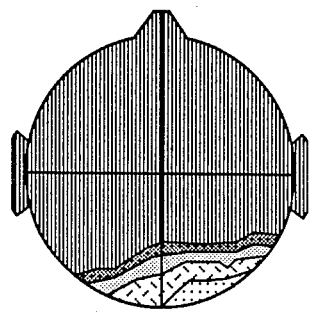
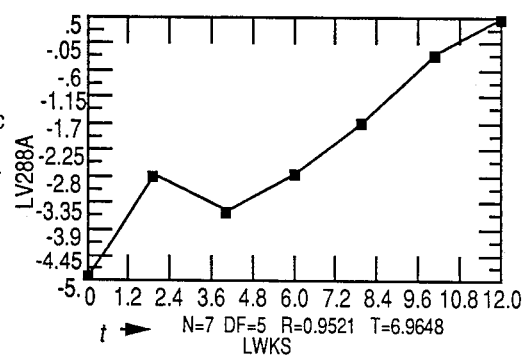
VER 288 Msec
TA →
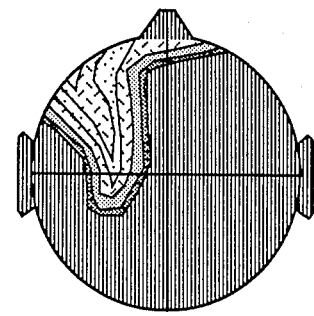
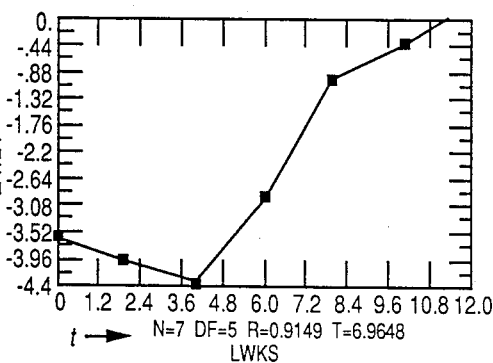
AER 124 Msec
TA →
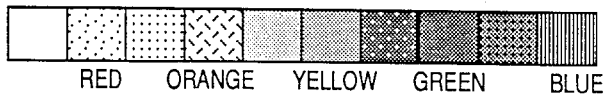
RED   ORANGE   YELLOW   GREEN   BLUE

FIG 10
SUBJECT FL
TREND ANALYSIS OF FEATURE DEVELOPED RETROSPECTIVELY BETWEEN THE FIRST AND LAST STUDIES-CONTINUED
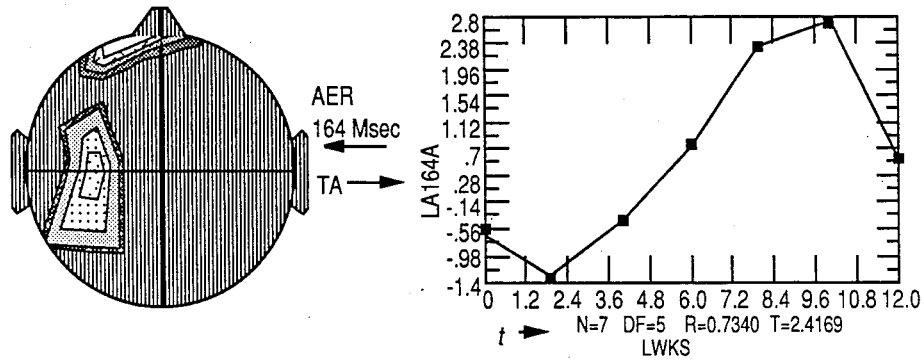
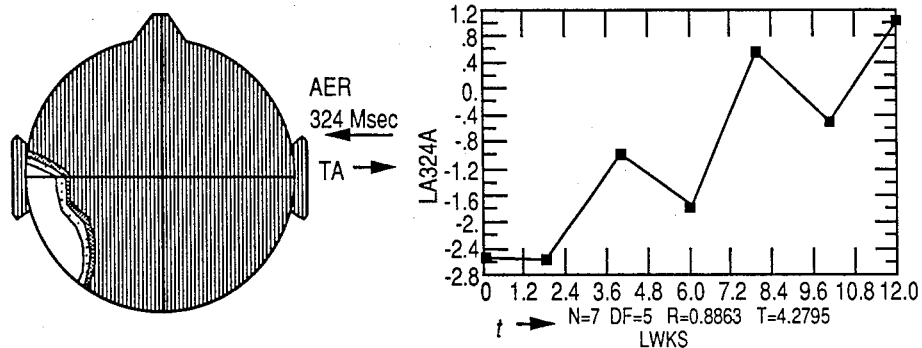
FIG 11
SUBJECT FL
PLOTS OF THE CROSS CORRELATION BETWEEN EYES OPEN DELTA RETROSPECTIVE FEATURES VERSUS NEUROPSYCHOLOGICAL (BEHAVIORAL) VARIABLES- RIGHT HAND TAPPING AND RIGHT HAND PEG BOARD SCORES
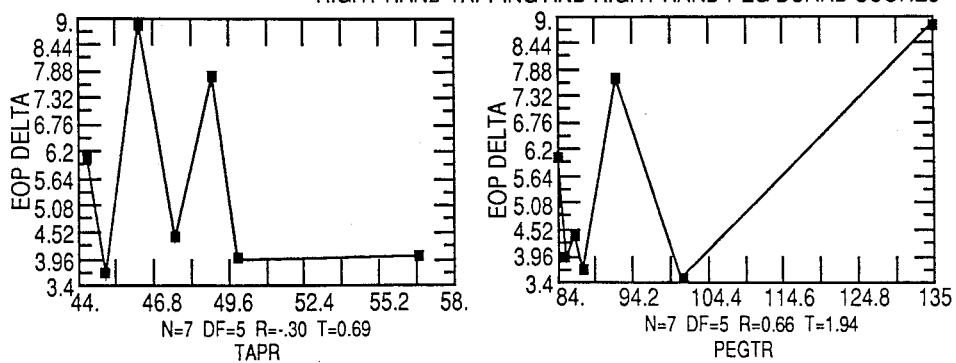

FIG 12
SUBJECT IC
TREND ANALYSIS OF FEATURE DEVELOPED BY COMPARISON OF INITIAL STUDIES TO CONTROL GROUP AND BEHAVIORAL DATA PLOTS AND COMPARISONS
TEMPLATE OR MASK
FEATURE TREND PLOTS
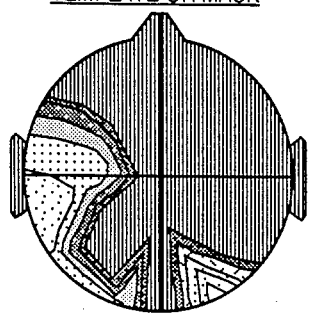
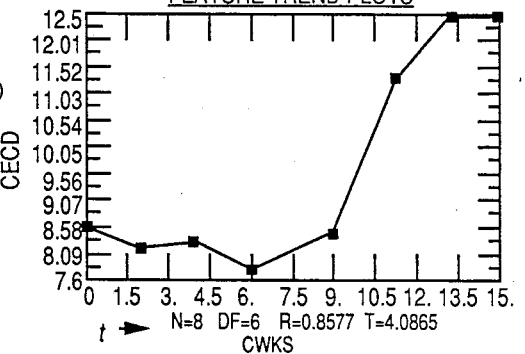
EYES CLOSED DELTA
← TA
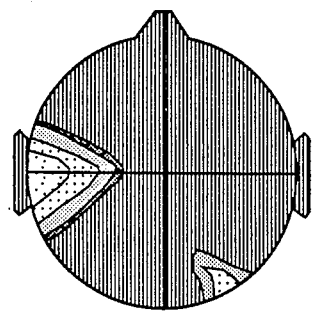
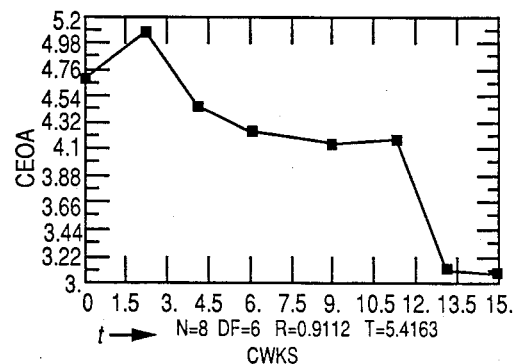
EYES OPEN ALPHA
← TA
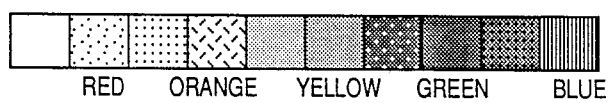
RED  ORANGE  YELLOW  GREEN  BLUE
BEHAVIORAL VARIABLES PLOTTED VS TIME
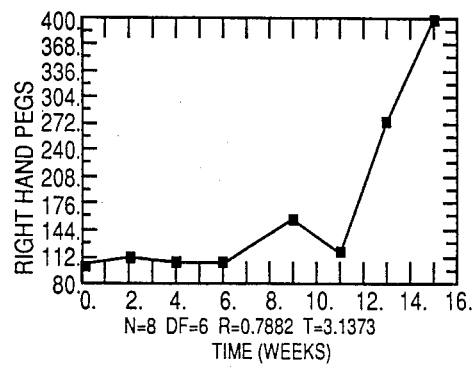
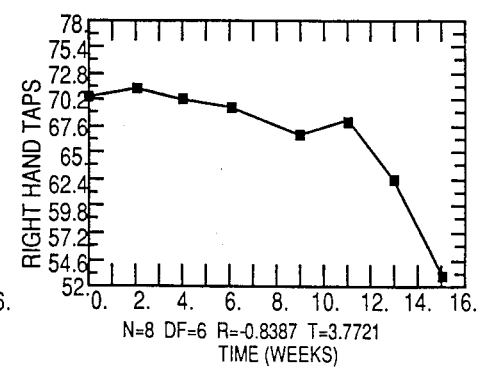

FIG 13
PATIENT JM
TREND PLOTS OF FEATURES DEVELOPED FROM
COMPARISON OF FIRST STUDIES AND CONTROL GROUP
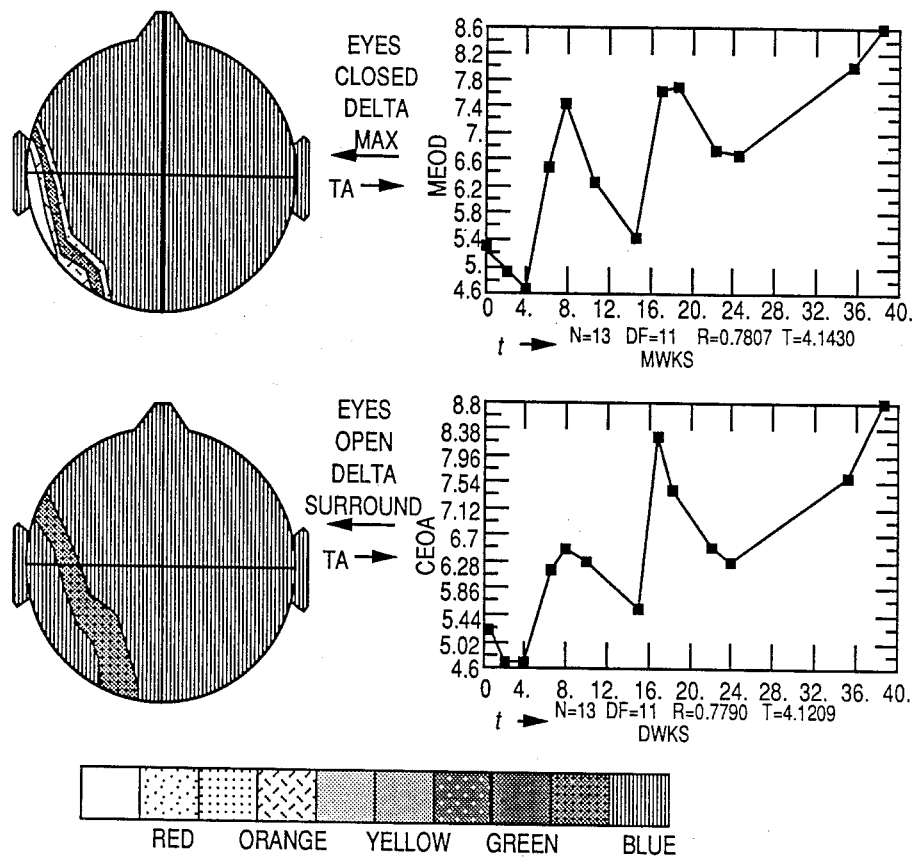
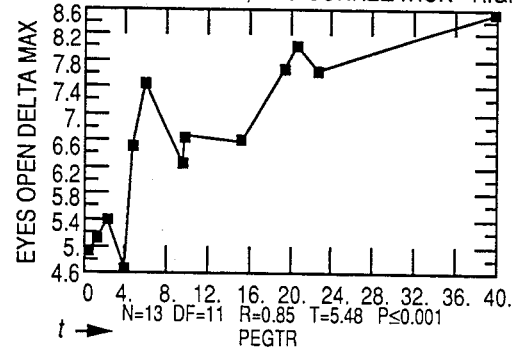
CROSS CORRELATION OF EYES OPEN DELTA FEATURE SHOWN ABOVE
WITH BEHAVIORAL FEATURE, PEG CORRELATION - RIGHT HAND FIG 14
PATIENT JM
TREND PLOTS OF FEATURES DEVELOPED FROM COMPARISON OF FIRST STUDIES WITH CONTROL GROUP- CONTINUED
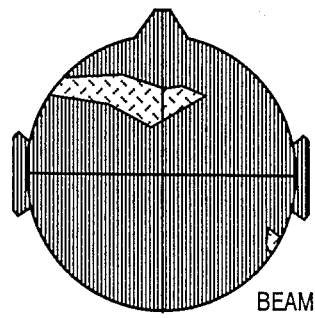
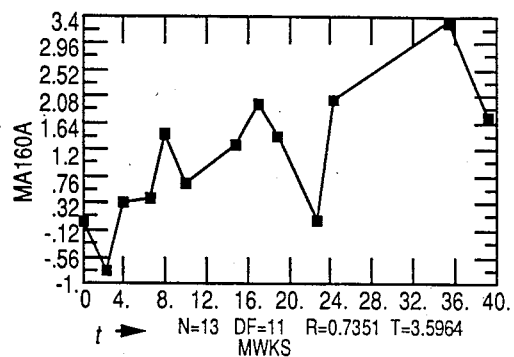
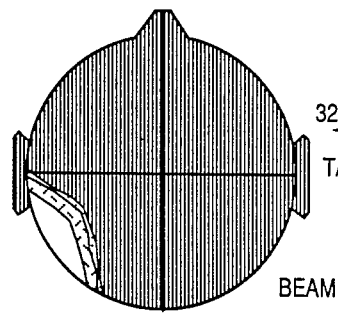
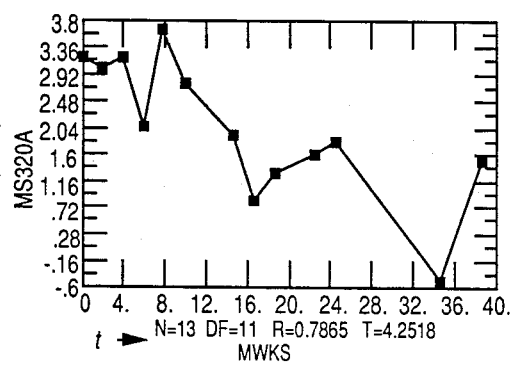
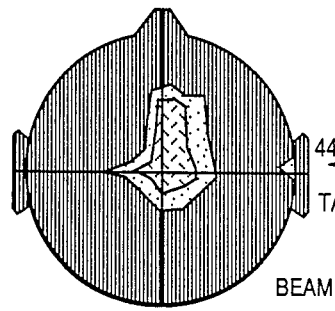
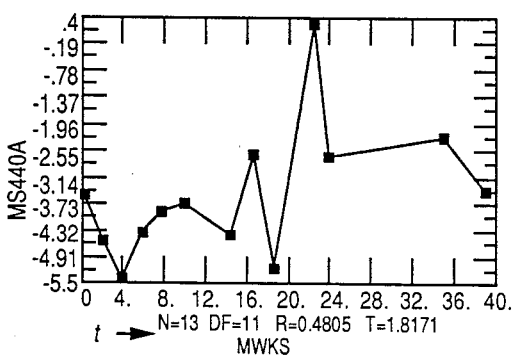
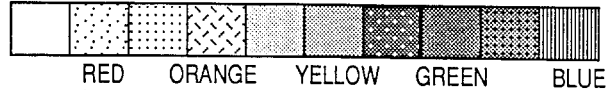

SUBJECT JM
TREND PLOTS FOR FEATURES DEVELOPED FROM APRIORI MASKS ALSO CROSS CORRELATION WITH BEHAVIORIAL VARIABLES

FIG 17
SUBJECT JM
TREND PLOTS FOR FEATURES DEVELOPED FROM APRIORI MASKS-CONTINUED
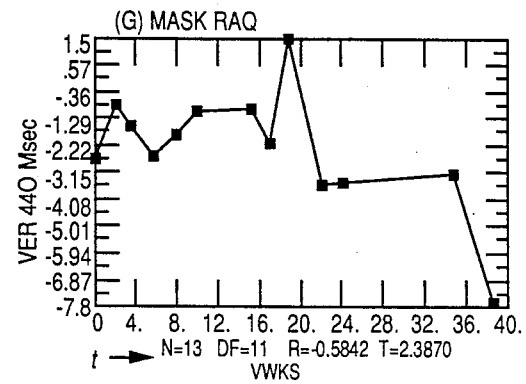
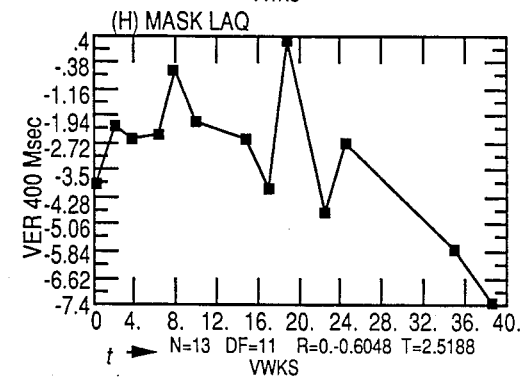
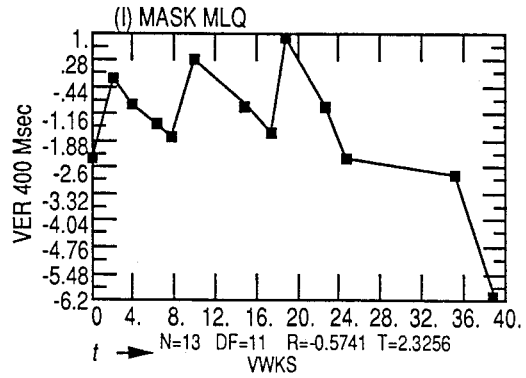

FIG 18
SUBJECT JM
MASKS AND TREND PLOTS FOR FEATURES DEVELOPED FROM MASKS IN TURN DEVELOPED BY COMPARISONS BETWEEN FIRST AND LAST STUDIES, I.E., RETROSPECTIVE ANALYSIS. T-SPM SHOWING CHANGE OVER OR NEAR TUMOR
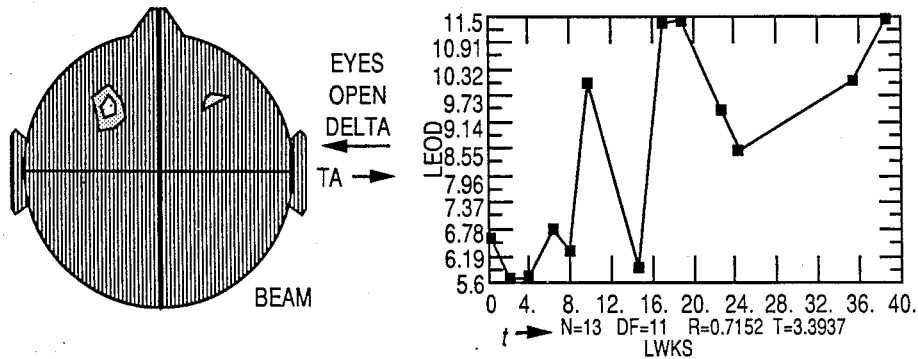
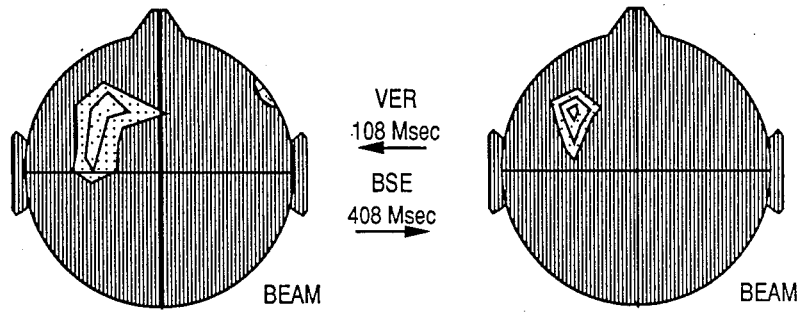
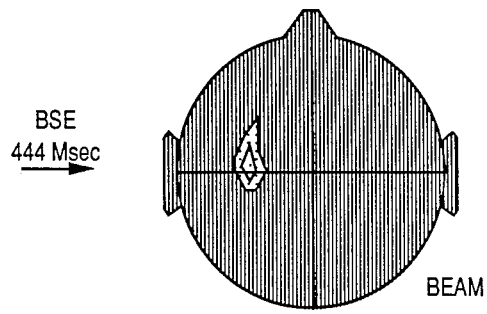
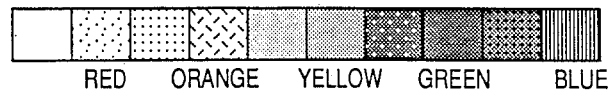

SUBJECT JM
MASKS AND TREND PLOTS FOR FEATURES DEVELOPED FROM MASKS IN TURN DEVELOPED BY COMPARISONS BETWEEN FIRST AND LAST STUDIES, I.E., RETROSPECTIVE ANALYSIS. T-SPM SHOWING CHANGE FROM THE TUMOR.

SUBJECT JM
FIG 20  TEMPLATE AND FEATURE DEVELOPMENT BASED UPON
REGRESSION AND CORRELATIONAL ANALYSIS-
EYES OPEN DELTA
SLOPE OF REGRESSION LINE
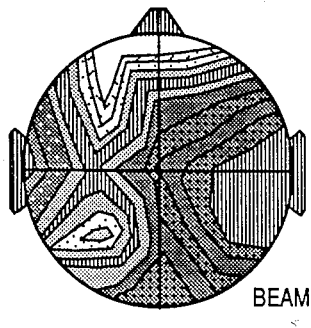
BEAM
CORRELATION COEFFICIENT
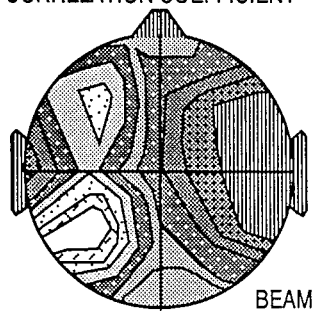
BEAM
SIGNIFICANCE OF REGRESSION LINE
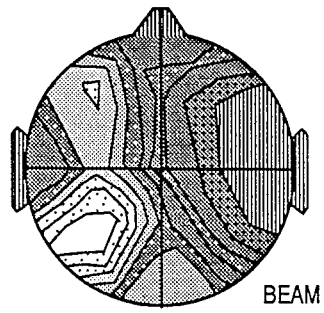
BEAM
TEMPLATE BASED UPON SIGNIFICANCE
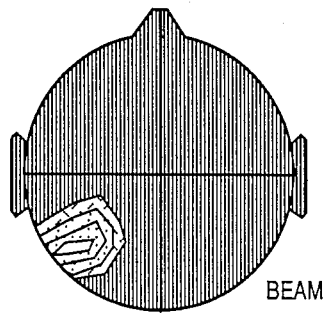
BEAM
TREND PLOT OF TEMPLATE
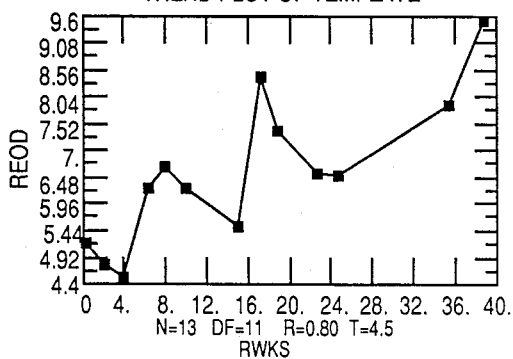
N=13  DF=11  R=0.80  T=4.5
RWKS
RED   ORANGE   YELLOW   GREEN   BLUE

FIG 21
SUBJECT JM
TEMPLATE AND FEATURE DEVELOPMENT BASED UPON REGRESSION AND CORRELATIONAL ANALYSIS-
EYES OPEN THETA
SLOPE OF REGRESSION LINE
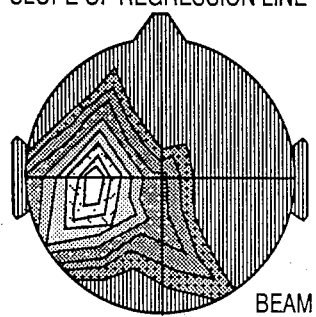
BEAM
CORRELATION COEFFICIENT
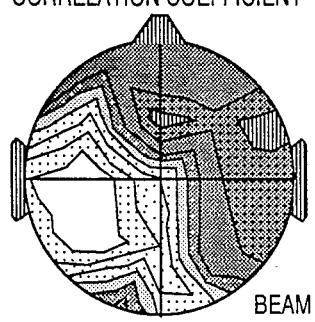
BEAM
SIGNIFICANCE OF REGRESSION LINE
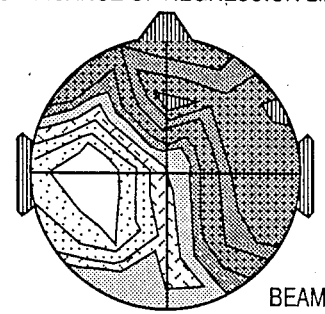
BEAM
TEMPLATE BASED UPON SIGNIFICANCE
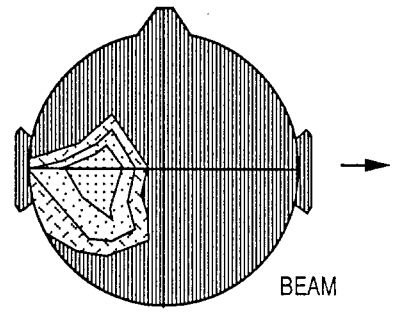
BEAM
TREND PLOT OF TEMPLATE
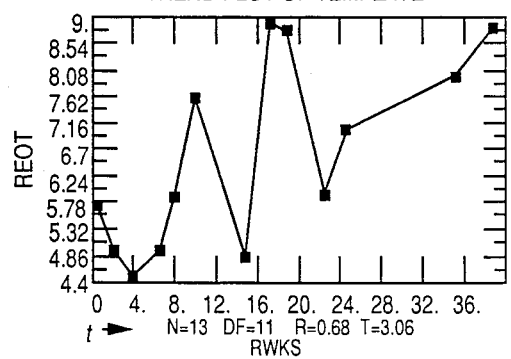
$N=13$  $DF=11$  $R=0.68$  $T=3.06$
RWKS
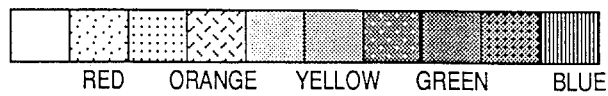
RED  ORANGE  YELLOW  GREEN  BLUE SUBJECT JM
FIG 22  ALTERNATIVE METHODS FOR THE FORMATION OF TREND PLOTS
A. DISCRIMINANT FUNCTION
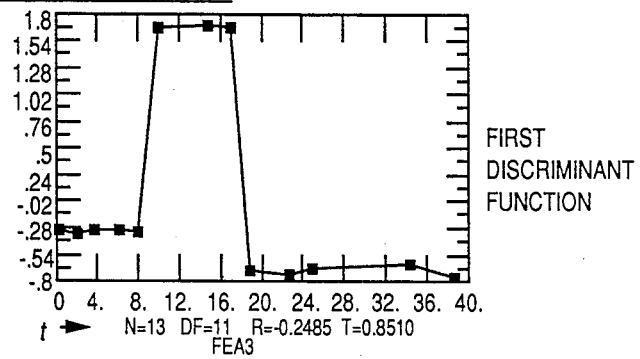
FIRST DISCRIMINANT FUNCTION
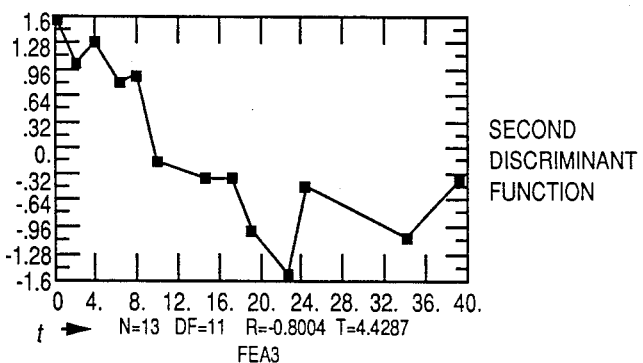
SECOND DISCRIMINANT FUNCTION
B. CROSS CORRELATIONAL ANALYSIS
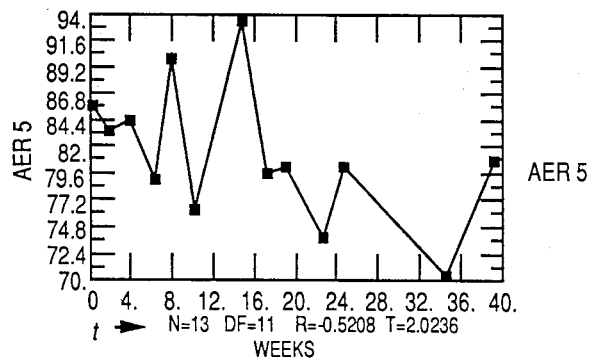
AER 5

TEMPORAL TRAJECTORY ANALYSIS IN BRAIN ELECTRICAL ACTIVITY MAPPING

BACKGROUND OF THE INVENTION

This invention relates to the measurement of brain electrical activity.

There is a need for early detection of brain abnormalities. For example, in patients in whom brain tumors have been treated, it would be desirable to detect recurrence of tumor growth as early as possible. Conventional techniques for detecting recurrence (behavioral tests, CAT scans, and NMR studies) typically are unable to detect recurrence until substantial tumor growth has occurred.

Brain electrical activity mapping (BEAM) is a known diagnostic tool for detecting brain abnormalities. BEAM is described in U.S. Pat. No. 4,421,122; Duffy et al., "Brain electrical activity mapping (BEAM): A new method for extending the clinical utility of EEG and evoked potential data," Ann. Neurol., 5:309–321 (1979); Duffy, Bartels, et al., "Significance Probability mapping: An aid to the topographic analysis of brain electrical activity," Electroenceph. Clin. Neurophysiol., 512:455–462 (1981); Duffy, *Topographic Mapping of Brain Electrical Activity*, Butterworths (1986) (all incorporated by reference).

SUMMARY OF THE INVENTION

In general the invention features the use of brain electrical activity mapping (BEAM) to generate trend plots tracking the long term change (typically a period of several weeks) of brain electrical activity within a region defined by a template. Changes in the trend plots provide an early indication of the recurrence of tumor growth.

To prepare the trend plots, the tumor (or other region of abnormality) is located using a BEAM-based statistical technique such as statistical probability mapping (described in Duffy, Bartels (1981), supra). Next, a template or mask is selected, preferably surrounding the tumor (in a "donut" like shape). A numerical "feature" is derived by summing the values of a BEAM image within the area of the template (using standard BEAM interpolation techniques to determine values within the template). The feature is plotted over time to produce a trend plot, from which recurrence of tumor growth can be observed.

The invention permits recurrence of tumor growth to be detected weeks earlier than is possible with conventional techniques. The invention has also proved useful in providing early detection of improvement in the condition of comatose patients.

Other features and advantages of the invention will be apparent from the following description of preferred embodiments and from the claims.

DESCRIPTION OF PREFERRED EMBODIMENTS

Drawings

FIGS. 2-22 show templates and trend plots for three clinical subjects.

Method

Figure 23:
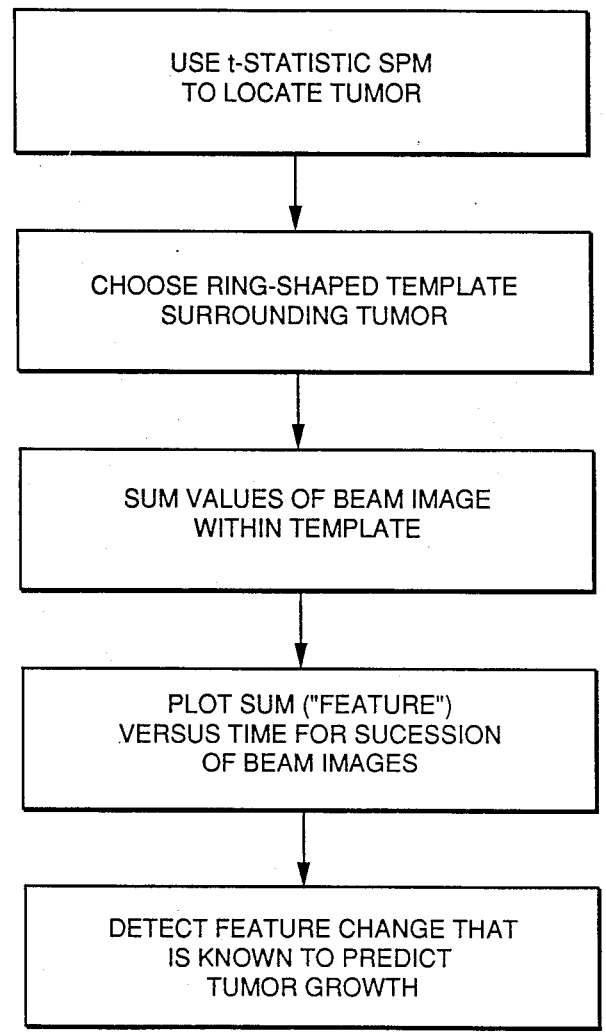
FIG. 23 is a block diagram summarizing one preferred procedure followed to prepare trend plots.

One preferred method for generating trend plots is shown in FIG. 23. First, the tumor (or other region of abnormality) is located using t-statistic statistical probability mapping ("SPM", described in Duffy, Bartels (1981), supra). Next, a template or mask is selected in the shape of a ring surrounding the tumor. The template is used to process BEAM data from tests repeated at weekly intervals; the BEAM image values within the area of the template (using standard BEAM interpolation techniques to determine values within the template) are summed to produce a number known as a "feature". The feature is plotted over time to produce the trend plot.

There are at least three preferred strategies available for choosing a template. The first technique is to compare the original subject's data with a control group, and define using the technique of significance probability mapping (Duffy, Bartels (1982), supra) the region above a t score of 2.0 where the subject differs from the control group. As this is the region of greatest abnormality, it can be tracked over time. However, one is interested not only in deviations from normal in this region but in adjacent areas. Accordingly, it is generally best to create concentric regions ("donut" shape) around the original region of abnormality. Concentric donuts are taken whose difference between their inner and outer radius is between ¼ and ¾ (preferably about ½) the diameter of the original abnormality reduced to roughly circular shape. In this way abnormalities can be detected of two sorts. If the lesion grows back in the same spot, it will be picked up in the initial abnormality template. If, on the other hand, that region remains constantly abnormal, but one or other of the donut shape regions surrounding the initial abnormality demonstrate deterioration, then it can be assumed that the lesion is expanding. Moreover, the rate of lesion expansion can be calculated by detecting when each successively more distant donut area deviates from its expected trajectory. By this technique, one can determine whether a lesion is growing in one place, or expanding, or both.

The second procedure is to decide on an a priori basis which areas one wishes to follow. Characteristically, the head can be broken into quadrants or further subdivided along known anatomical boundaries by the creation of a template or series of templates.

The third technique is a retrospective procedure where one follows a subject for a period of time and then performs a retrospective analysis to locate regions which appear to be changing. For example, if a subject is studied over three or more times, preferably 10 or more times, then a one-way analysis of variants can be performed for each electrode. The resulting F statistic can be plotted and regions above a criterion level at the .05 probability point can be defined as "templates". One then can plot the change of value under the template to determine whether or not the trajectories are showing a monotonic increase or decrease, a finding of interest. If any regions are found of interest, these can then be followed prospectively.

In short, there are three ways to choose templates. In the first, one defines the region to be followed by the region that is already abnormal at the beginning of the study, or that had been abnormal prior to the beginning of the study. Second, one can define regions on some a priori basis by simply creating templates where one wishes. Thirdly, one can retrospectively examine a subset of sequential studies to define regions where change is in fact occurring, and then follow those prospectively.

CLINICAL RESULTS

Over a two year period we studied 24 subjects with treated glioblastoma multiforme ("GBM") for recurrence. Our longest complete study epoch for one subject spanned 40 weeks and the shortest 6 weeks. We have also followed 10 normal control subjects an average of 10 sessions each. The overall goal is to detect when the data of a patient being followed over time begins to deviate from what might be predicted, thereby forecasting a recurrence. The process by which one starts with raw neurophysiological data and ends with a statistical determination of recurrence can be thought of as involving four steps: (1) generation of numerical measures or "features", i.e., how one produces "numbers" from EEG and EP data that can be followed over time; (2) feature selection, i.e., how to select, from all features created, those to be used in making predictions; (3) rule generation, i.e., how the selected features are made into diagnostic rules; and (4) rule testing, i.e., how to evaluate the clinical value of such rules.

Figure 1:
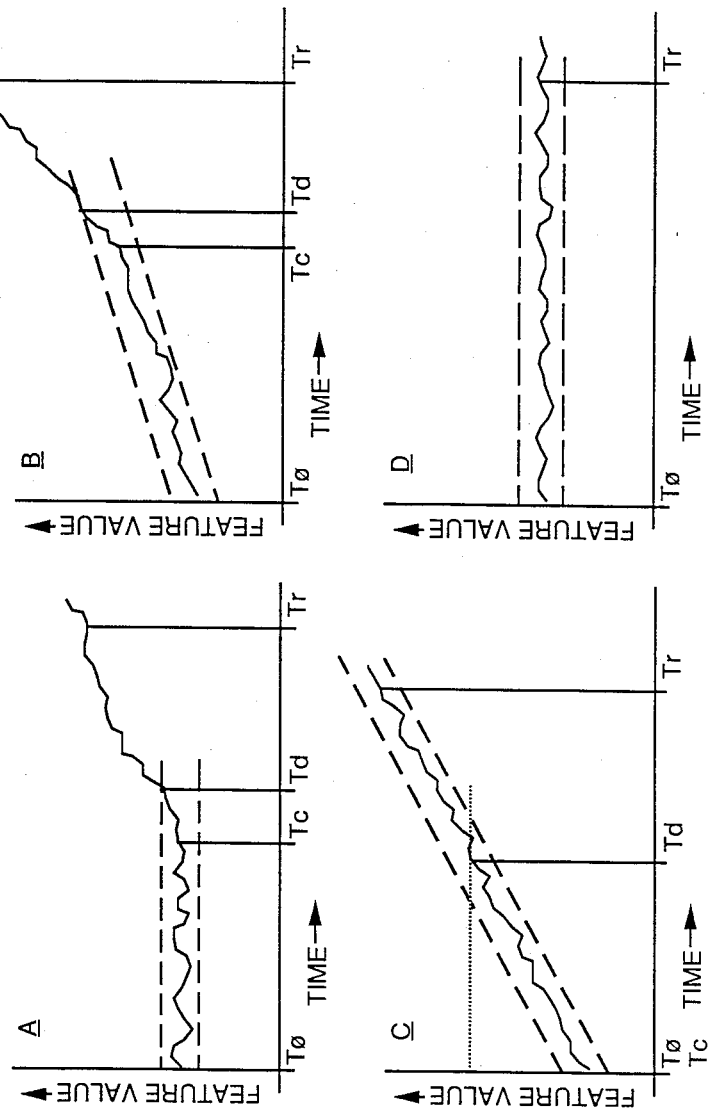
FIG. 1 shows four examples of trend plots.

We have processed all data on 18 subjects and have developed features and plotted their trends over time. Such trend plots form a basis for statistical prediction of recurrence. Four hypothetical trend plots and how predictions might be made are illustrated in FIG. 1. Time zero (TO) references a subject's entry into our study. Tc refers to the point in time at which a feature begins to deviate from its previous track; Td refers to the time this deviation is statistically detected. Tr refers to time of clinically recognized GBM recurrence. To be of value Td must occur before Tr and as close to Tc as possible.

A goal of our present and proposed effort is the development of neurophysiological measurements or "features" capable of describing change in neurological state over time. A second goal is to detect, in various neurological pathologies, at what point in time a feature value deviates from "expected" values. There are, essentially, four likely possibilities; the hypothetical trend plots of feature vs. time are shown in this figure.

In A, the feature value initially remains relatively constant (zero slope), but then rather suddenly begins to increase (positive slope). One might imagine this to exemplify a situation where a de novo, progressive process suddenly begins to cause a changing clinical neurophysiological picture. The time of such change is labeled Tc. Time Tc can, of course, only be determined retrospectively. However, a change in slope can be detected by a significance test where each new data point is determined to be within or outside previously determined statistical limits. In A, statistical detection of recurrence would occur at some time (Td) when the feature exceeds some predetermined confidence limit (shown as dotted horizontal lines). A simple t-test might suffice for this test. For Td to be of clinical use it would have to precede the time of detection of change (Tr) by other clinical methods. Td should be as close to Tc as possible.

In B, a similar process is shown, however, the change at Tc occurs not on a stable, but a gradually increasing background. This is what might be seen in a neurological condition which is already in a state of change at study onset (TO), but this change accelerates at Tc. Regression analysis can provide the confidence limits to statistically detect (Td), the point at which there was a significant change in the rate of progression.

In C, there is already clear change present at TO (positive slope) which continues without alteration to Tr. This is what might be expected late in a patient's course (e.g., as portrayed in the right half of A or B) whose clinical course and electrophysiological data are unchangingly progressive. Here one might wish to set some a priori threshold and if the feature value passes this limit, Td will have occurred. This would be a difficult situation to handle, statistically. In such a patient one might want to search for other features. Such features as shown in C may occur in patients whose clinical course is apparently constant, i.e., there need not be exact correspondence between clinical and electrophysiological trends.

In D, the feature value remains constant from TO to Tr, failing to show Tc and, of course, Td. This would not be a clinically useful feature.

Of course, many other possibilities may occur. For example, slopes may be negative rather than positive, slopes may go from negative to positive or visa versa (a V or U shape), and variable amounts of noise or scatter may obscure trends.

To illustrate our complex but fruitful findings we shall detail three representative subjects. Subjects FL and IC both entered our study in radiographically and clinically stable condition following intracarotid BCNU therapy for their GBM. Their clinical recurrence (Tr) was relatively abrupt and was not predicted by usual clinical means. As such, subject FL probably exemplifies the majority of patients at risk for recurrent GBM following their first treatment. Subject FL was a 65 year old male with a glioblastoma multiforme of the left temporal lobe verified by a microbiopsy in February. He was treated by radiation and intra-carotid BCNU chemotherapy in March and admitted to our study in late May (TO) at which time his clinical course was stable and his post-treatment CT scan demonstrated reduced mass effect with residual left temporal lucency. Time of recurrence (Tr) was placed at $T=11$ weeks at which point the CT scan demonstrated mass effect with a 5 mm displacement of midline structures to the right. The subject was retreated in September, responded well initially, but recurred again and expired in December. This subject exemplifies a rapdily growing, quickly recurring GBM.

Subject IC may exemplify a patient in her second remission, still relatively early in the course of her disease.

The third subject, JM, entered our study eight years after initial diagnosis and treatment. In the interim she suffered many recurrences. Following her first intracarotid BCNU injection (most recent therapy) she responded very well with remission of most symptoms and involution of tumor on CT scan. Nonetheless, it was clearly anticipated that her course would be relentlessly progressive and that this would probably be her last period of remission. She constitutes the special case of a patient in the end stage of the disease and in a final remission.

Our first approach was to form a BEAM t-statistic SPM (Duffy, Bartels (1981), supra) comparing the subject's first three sessions to an age appropriate control group. Such t-SPM delineate regions of between group difference. Templates or masks were then formed from the t-SPM using as a t cutoff point the top 25% of t above t=2.0. These templates were then used to generate features from each study session. The features generated were plotted against time (see FIGS. 2 and 3) to show trend patterns. This approach develops features from data available at the onset of a study and evaluates their change with time. Most features generated type A and B trend plots [EOP delta, ECL delta (FIG. 2), and AER 152 (FIG. 3)]. Trend plot patterns, as used in this study, are defined in FIG. 1. Note that by 8 weeks a clear trend can be detected in EOP delta and ECL delta feature plots. Although noisy, AER 152 suggested an even earlier worsening. In contrast, EOP theta (FIG. 2) and EOP beta 3 (FIG. 3) showed the gradual progression typical of the type C trend plot.

In virtually every tumor case, but not in controls, it has been possible to demonstrate type C trend plots even when no other evidence of clinical progression exists. This suggests that some neurophysiological features are sensitive to the slow but relentless process that must be ongoing even when such patients are clinically and radiographically stable. Type A and B features are more useful for the prediction process. Their abrupt changes in slope may signal a threshold effect crossed, perhaps, as more functionally important regions become involved.

FIGS. 2 and 3 illustrate the process by which one can neurophysiologically follow a subject over time. The top illustration in FIG. 2 is a BEAM t-statistic SPM formed by comparison between two groups. The first group was our 22 member 60 to 69 year old optimally healthy control population. The second was formed from the first three sessions of subject FL starting at T0 and extending to just under 4 weeks. Such t-SPM graphically delineate regions where subject FL differs from normal. The top illustration in FIG. 2 shows a schematic outline of the head in vertex view with left ear to the left, right ear to the right, nose above, and occiput down. In this case the maximal t-value was 7.02. This t-SPM was formed in the eyes open state for EEG delta activity (0–3.8 Hz). The next step in the analysis process involves forming a template or mask from this t-SPM using a lower t cutoff value of 3.26. The range of 3.26 to 7.02 represented the upper 25% of t-values over a t of 2.0. The resulting template is shown at the top of the left column labeled "EOP delta". This template was then used to generate features, one from each of FL's seven studies. The numerical values in the matrix underlying the BEAM image of EOP delta are summated to form a single number (feature). Immediately adjacent to the EOP delta mask is a trend plot (labeled TA for trend analysis) in which the feature value is plotted against time (weeks) for each of FL's seven studies.

This process is repeated for five other states, eyes closed (ECL) delta, eyes open (EOP) theta (4–7.8 Hz), EOP beta 3 (20–23.8 Hz), auditory evoked response (AER) from 316 through 356 msec, and AER from 152 through 192 msec. In the illustration, the template and the trend plot of the feature formed from that template are displayed adjacent to each other.

Note the sharp upward deflection at 6 weeks for EOP delta, ECL delta (FIG. 2) and at 3.8 weeks for AER 152 (FIG. 3). These would be type A and/or type B features according to the classification scheme outlined in the legend of FIG. 1. Note the somewhat noisy, but mostly continuous change of features EOP theta (FIG. 2), EOP beta 3 (FIG. 3), and AER 316 (FIG. 3) as demonstrated in the trend plots. According to the same classification scheme these would approximate type C features.

On the basis of the A and B features, recurrence sometime between week 3 and 6 might be postulated. On the basis of the type C feature a long-term trend might also be operating. In any event these features appear much more indicative of worsening than do behavioral variables.

Clinical recurrence (Tr) for FL came rather abruptly at 11 weeks. Behavioral predictors including right handed motor tasks failed to anticipate this clinical decline. Simple t-SPM neurophysiological feature trend plots, however, were able to show inflection points and thereby forecast recurrence at least 3 weeks before Tr.

Figure 4:
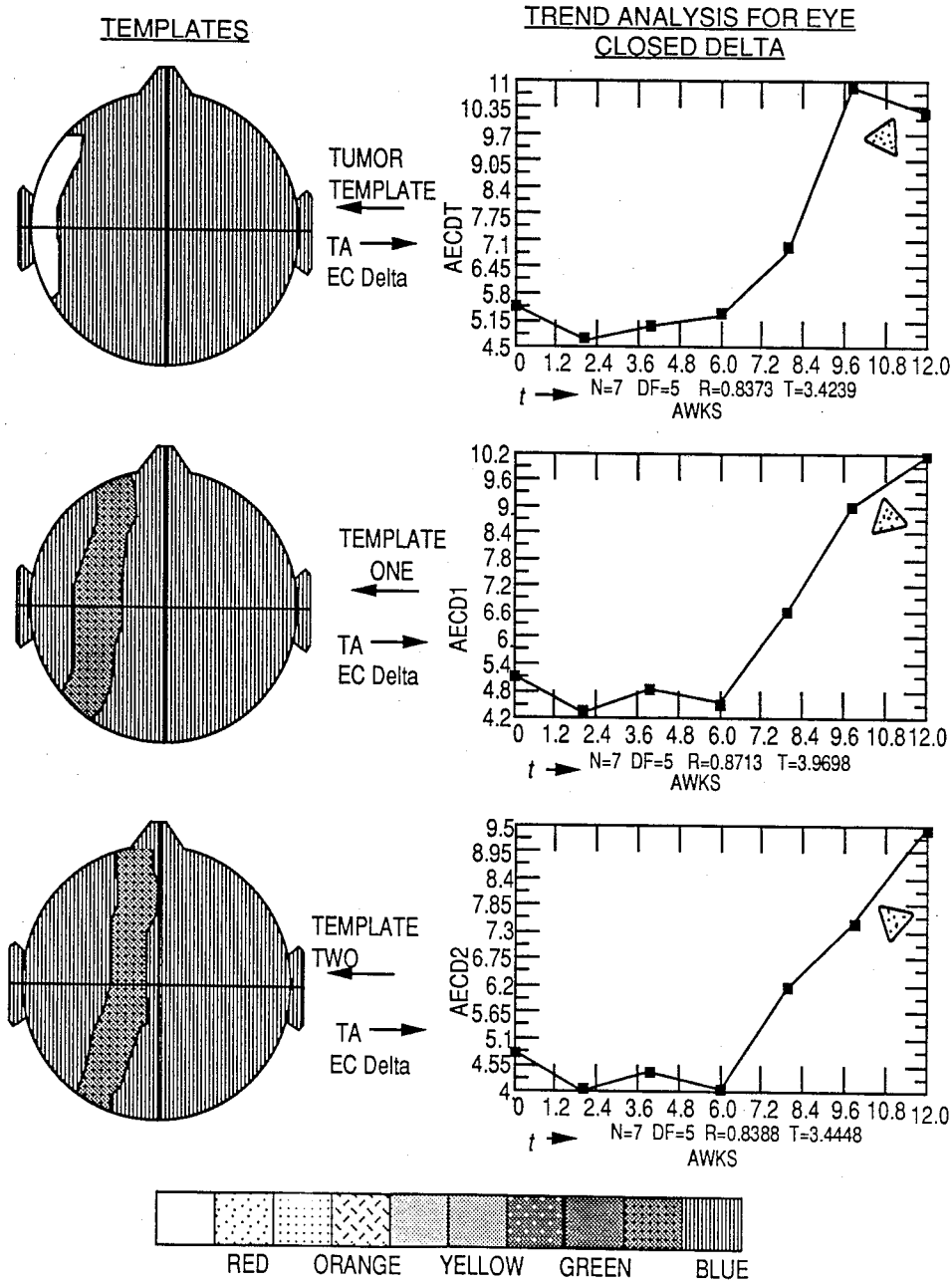

To investigate the peculiar and abrupt late flattening of the EOP and ECL delta trend plots (see arrow FIG. 2), we created, by hand, a series of templates overlying the tumor and progressively more distant (FIGS. 4 and 5). Note (arrows) that for the template regions increasingly distant from the tumor, this flattening lessens. We believe that this may represent a "saturation" effect where regions reach a point where no more delta can be produced. This finding suggests that templates directly overlying the region of primary abnormality may not detect change, in advanced pathology, as well as features developed from more distant regions where saturation has not yet occurred.

Templates were constructed "by hand" based upon inspection of the CT scan. The "tumor" template represented the region felt most likely to overlay the lesion itself. Progressively adjacent regions formed templates 1 through 4 as is illustrated in FIGS. 4 and 5. These templates were then used to develop features and these, in turn, formed trend plots. Features were developed from many states. FIGS. 4 and 5 illustrate the trends for the eyes closed (ECL) delta (0–3.8 Hz) state.

In FIGS. 4 and 5 note the relative feature value change for the next to last sessions as highlighted by the red arrow. Overlying the lesion ECL delta decreased, but as one moves progressively away from the tumor (see templates 1–4) a reverse relationship develops, i.e., the last sessions shows progressively more delta. We believe this interesting relationship can be explained by two phenomena. The first we refer to as "saturation" and the second "contiguous spread". It seems likely that as pathology progresses there is a finite limit to the amount of delta that can be produced in any one region. At some point delta plateaus and may even lessen as the destructive process continues. This may explain the decline shown in the trend for the tumor-template generated features (first illustration FIG. 4). This process we refer to as "saturation".

Figure 6:
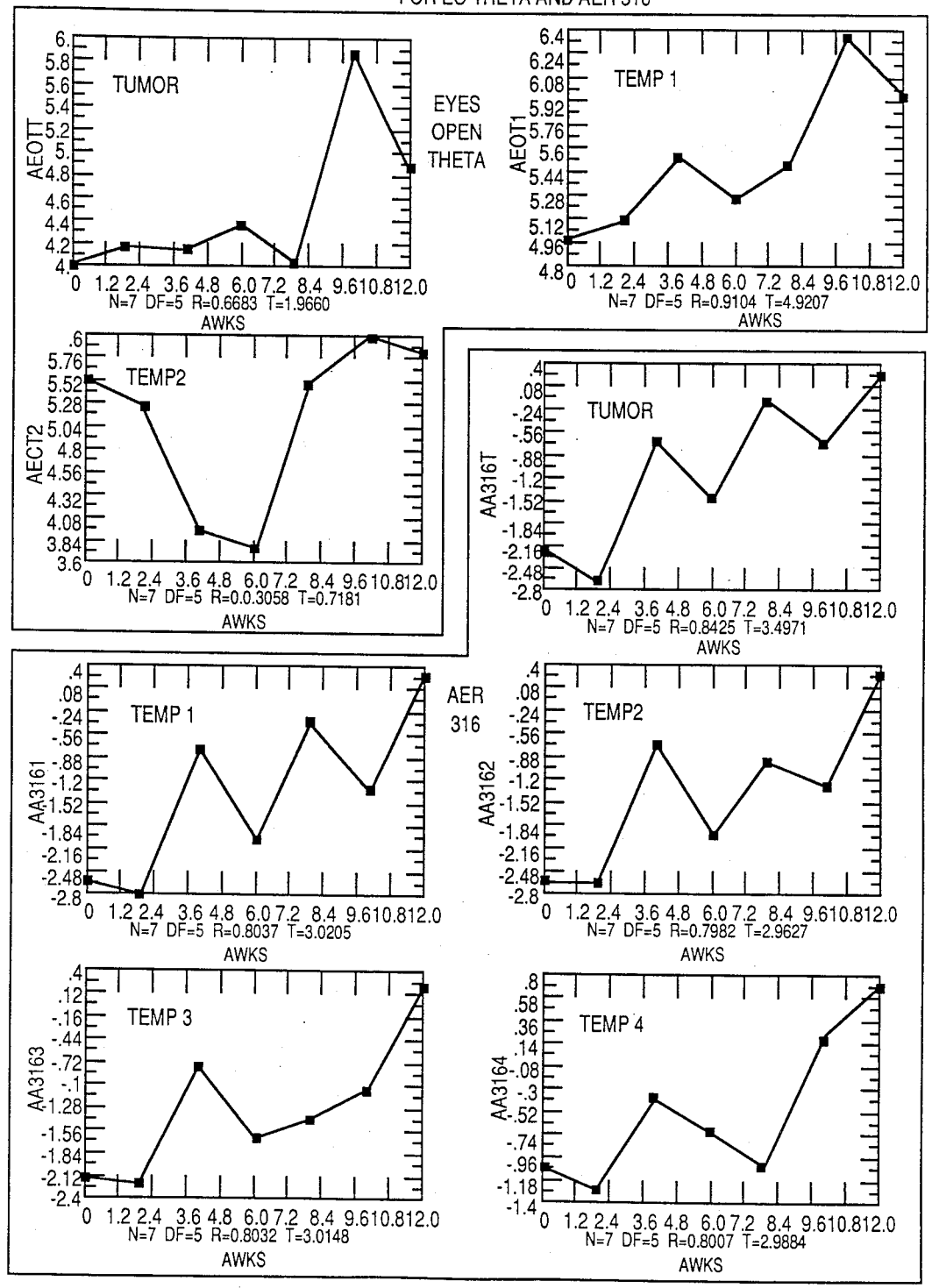

FIGS. 6 and 7 demonstrate the complex interaction between feature type and distance of the corresponding template from the primary pathology. For example AER 316 (FIG. 6) and AER 152 (FIG. 7) show the same type C trend plot for all templates becoming only noisier with distance. In contrast, EOP theta (FIG. 6) shows type A over lesion, type C adjacent to the lesion, and type D further away. The reasons for these differences are not yet clear. However, it does appear that EP features are more sensitive at a distance than features of EEG origin—except in cases where there are extensive lesions. The change in trend plot with distance is probably a complex interaction of threshold, contiguous spread, saturation, and data type.

As a lesion progresses, it may manifest itself not only by increased abnormality overlying the lesion, but also by inducing electrophysiological abnormality at increasing distance from the original lesion. This process, which we call "contiguous spread" would lead to a gradient of abnormality away from the lesion. Regions more distant would be less involved with the abnormality and less likely to approach "saturation" by Tr. This may also mean that distal regions, late on in a subject's course, may provide better indices of change than more proximal ones. The saturation effect may also be operating for the last two points of EOP theta (FIG. 6) and AER 152 (FIG. 7).

Not all features show similar change with distance from the lesion. For example AER 316 (FIG. 6) shows a type C trend plot, with some superimposed noise, that differs little from the tumor to template 4. AER 152 (FIG. 7) remains type C, showing some saturation effect and some noise especially in template 4. EOP theta, however, differs radically with tumor proximity (FIG. 6). It shows a somewhat late type A response over the lesion, type C response adjacent to the lesion (template 1), and noisy type D response further away (templates 2-4, only 2 is shown). The importance of looking not only directly over a lesion, but adjacent to it is no better illustrated by EOP theta. Early, albeit type C, change evident under template 1 would have been missed by study limited to the tumor template. The interaction of feature type and spatial location may be quite complex.

To determine, retrospectively, which regions actually demonstrate the largest change over time, a two group comparison was made of FL's first 3 studies against his last three studies by the t-SPM, template, feature trend plot method previously described (see FIGS. 8, 9, 10, 11). The primary finding was that regions around and near, but not directly over the initial lesion produced templates and, in turn, features most descriptive of neurological change. This would support the hypothesis that contiguous spread of abnormality is as important an indicator of change as increased abnormality at the original pathological locus. As was the case in "prospective" analysis (first studies versus control group comparison), trend plots for this retrospective analysis demonstrated both continuous progressive change (type C: EOP beta 2, EOP beta 3, VER 288, AER 164, AER 324) and sudden shifts (type A: ECL delta, AER 124); (type B: EOP delta) as shown in FIGS. 8, 9 and 10. No one of these features correlated significantly with the behavioral variables (see FIG. 11). In general, for patients in their first remission there were poor correlations between neurophysiological features and behavioral variables.

Samples of the neurophysiological and behavioral data of subject IC, in her second remission, are shown in FIG. 12. Subject IC was a 44 year old female who had a left parieto-temporal GBM diagnosed and treated elsewhere by radiation and CCNU 1 year before entry into our study. Six months later (January) she was treated with BCNU for a clinical recurrence. She entered our study in September at which time her CT scan had been stable showing a markedly reduced mass effect and diminished edema. In October the CT scan showed improvement and her clinical state was stable. She suffered rapid clinical deterioration in January, 14 weeks after entry into our study. Retreatment prolonged her life by 11 months when she finally succumbed. The postmortem neuropathological report demonstrated "recurrent left hemisphere gliosarcoma". This subject showed a rapidly growing and quickly recurring GBM.

Tr was at 14 weeks. Many feature trend plots showed Tc at 9 weeks and Td by 11 weeks (e.g., type A: ECL delta). Other features showed a gradual decline with late worsening (e.g., type B or C: EOP alpha). Behavioral variables did show change in advance of Tr but only by one week. Behavioral and neurophysiologic data were not significantly correlated. Note that useful templates delineated regions over and also remote from the initial lesion. ECL delta demonstrated "saturation".

Two representative templates are shown, developed from t-SPM which were formed from a two group comparison. The first group consisted of subject ICs first three studies done during a period of relative clinical stability. The second group consisted of a control population of optimally healthy adults, ages 40 to 49 years. The templates were chosen using a t cutoff delineating the top 50% of t values above a t of 2.0. Features were formed and plotted over time as previously described. In FIG. 8 the templates and trend plots for ECL delta and EOP theta are shown. FIG. 8 also shows the trend plots for behavioral variables derived from right hand (left hemisphere) function.

Note that the templates delineate prominent regional difference not only overlying or adjacent to the tumor, but also over the contralateral hemisphere. The trend plot for ECL delta shows an abrupt change beginning at 9 weeks and very evident by 11 weeks (type A response). EOP alpha suggests a mild decrement starting at 4 weeks, continuing to 11 weeks and then abruptly dropping (type B response). The behavioral variables demonstrate change starting at 11 weeks becoming very evident by 13 weeks.

Thus, both the electrophysiological and behavioral variables showed change in advance of clinical recurrence at 14 weeks. The electrophysiological changes appeared about two weeks in advance of the behavioral changes and about 4 weeks in advance of Tr.

Subject JM was studied during her eighth remission. JM was a 33 year old female whose left frontal GBM was first discovered and treated 7 years before entrance into our study. Initial therapy consisted of surgical excision followed by radiation. Beginning several years later she was treated every 6-12 months with chemotherapy, initially with systemic CCNU and later BCNU. She entered our 39 week study in June one month following intracarotid BCNU therapy at which time she was relatively stable and her CT scan demonstrated absent mass effect with no contrast enhancement. The left frontal horn was dilated. This subject represents a very difficult and complex patient, late in her clinical course following many recurrences, whose clinical state may appear stable, but whose neurological condition is slowly, but relentlessly worsening.

Data from her first three studies compared to control group are shown in FIGS. 13 and 14. Note that the template surrounding the lesion (EOP delta-surround) produced a slightly smoother type C trend plot than did the template overlying the primary region of initial group difference (EOP delta-max). This again emphasizes the value of templates near, but not directly over initial abnormalities. In contrast to the previous subjects, the correlation between neurophysiological features and behavioral variables was high and very statistically significant (see EOP delta-max vs. PEGTR, FIG. 13). The apparent "noise" perturbations in the EOP delta-max trend plot at 8 and 17 to 20 weeks were mirrored by comparable decline in behavioral performance. In general behavioral and neurophysiological variables correlated only in the face of rapidly progressive pathology such as that seen near the end of a period of remission or in subjects in or near their final period of remission. As for the previous subjects, both type C (EOP delta-max, EOP delta-surround, AER 160, BSE 320) and type A (BSE 440) trend plots were demonstrable. In general, however, type A responses were more difficult to demonstrate late during a patient's remission or in patients with multiple remissions. When found in such patients, type A trend plots were previously obtained from regions away from maximal initial abnormality (see BSE 440, FIG. 14) and more often from EP data.

FIGS. 13 and 14 show t-SPM generated templates and their corresponding trend plots obtained by comparison of JM's first three studies (considered as a group) against a normative control population of 30 to 39 year old adults. Templates were made from the top 25% of t-value over t=2.00. Templates were also constructed from the t-SPM from the next 25% range of t over 2.0, i.e., from 50% to 75% of t over 2.0. These were formed to investigate whether features sensitive to enlarging regions of abnormality were more important than features regionally keyed to the primary abnormality.

Relatively little difference, for JM, was found between trend plots of features formed over the maximum abnormality and those from a surround. Both EOP delta-maximum and EOP delta-surround features showed similar type C trend plots (see FIG. 1). However, both plots show a great deal of "noise". By visual inspection the wave shape of the EOP delta trend plot (FIG. 13) was quite similar to the behavioral trend plot (right hand peg board). Thus, a cross correlation between EOP delta and PEGTR was formed and is shown below in FIG. 13. The electrophysiological features and behavioral feature were very highly correlated (r=0.85, p<0.001). This suggests that the delta peaks at 8 and 20 weeks may have corresponded to real, but transient clinical worsening.

Most features demonstrated type C progression. One exception was BSE 440 (FIG. 14) obtained from the central region in response to bilateral somatosensory stimulation over the 440 and 480 msec latency epoch. It seemed to show change occurring between weeks 16 and 20 which then persisted to week 40, i.e., more a type A or B response albeit "noisy".

Figure 15:
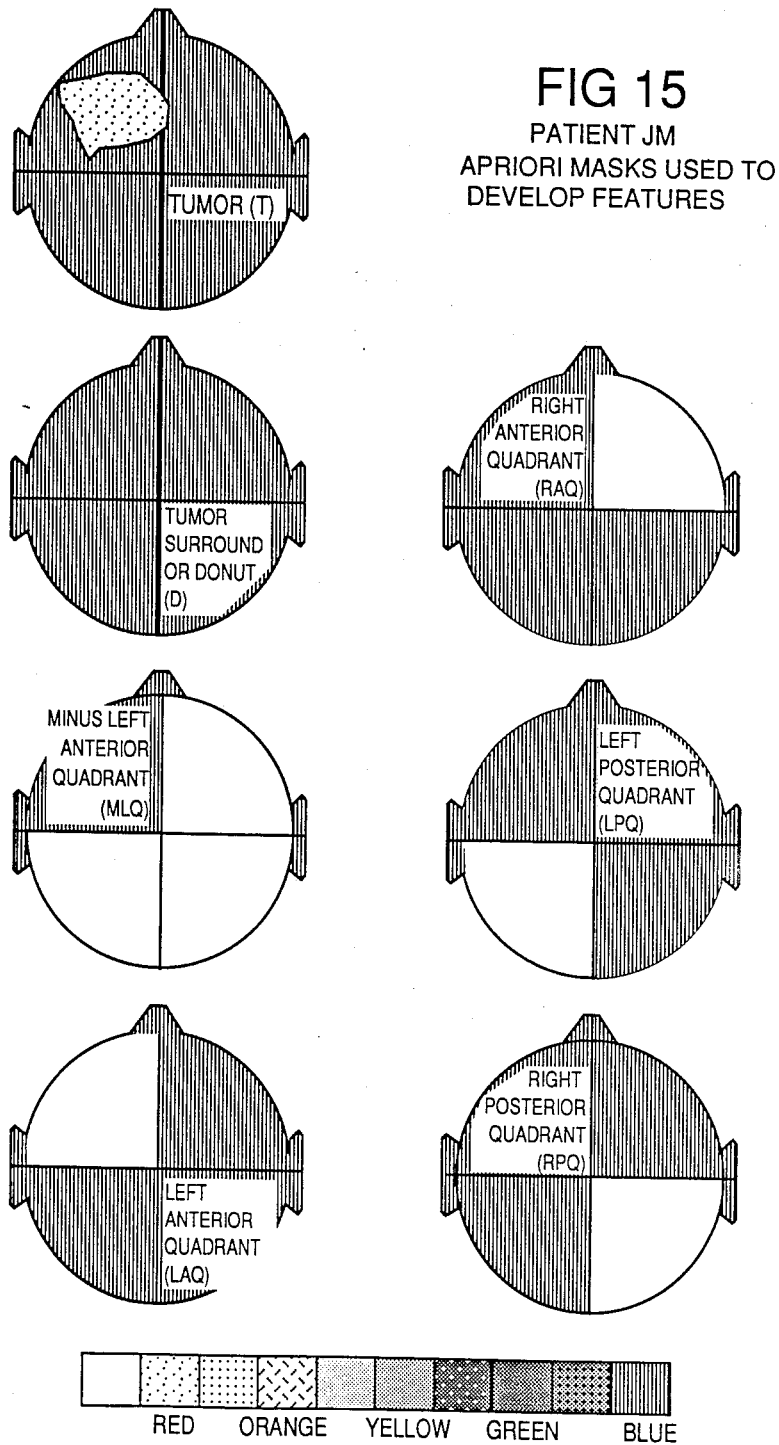
Figure 16:
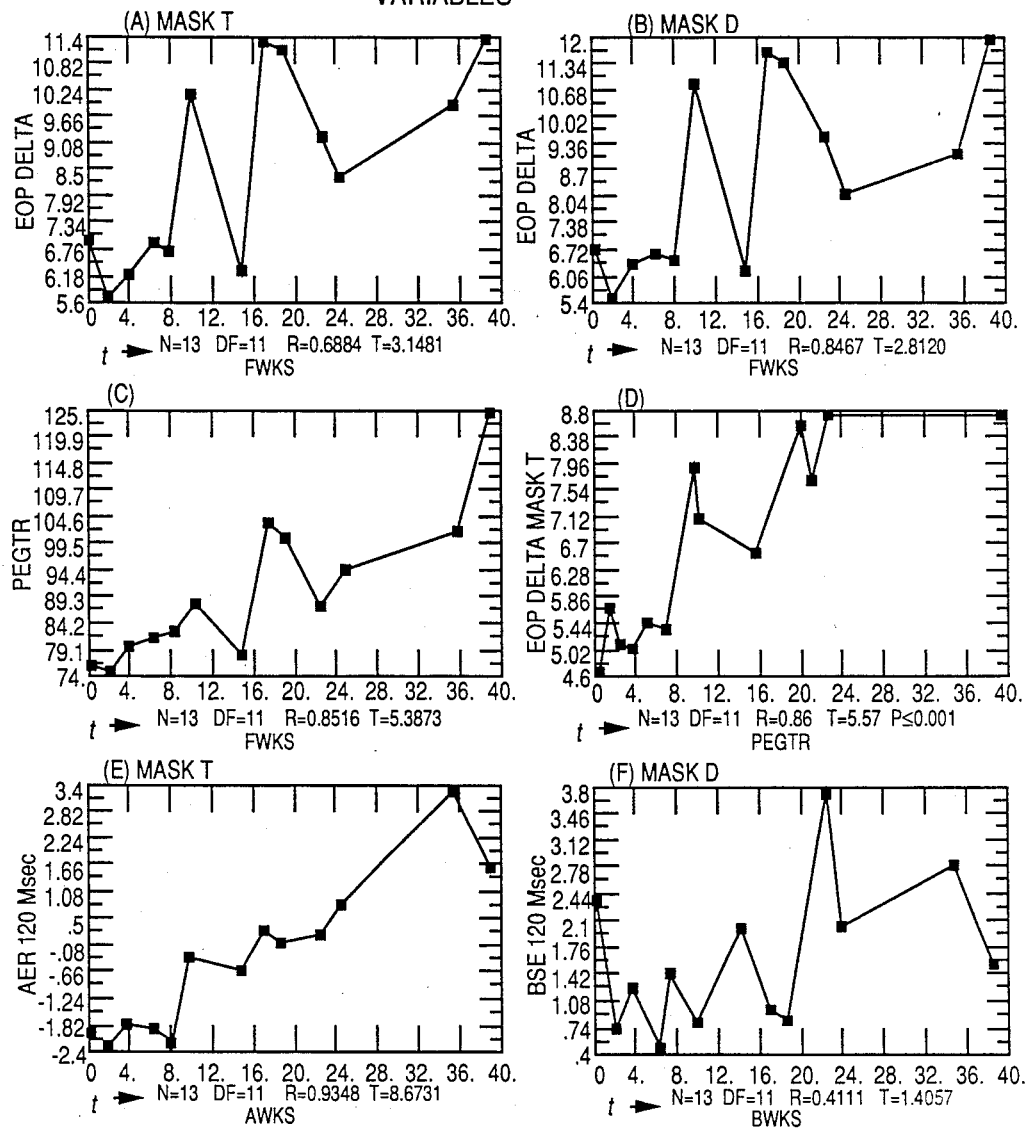

To investigate the spatial relationship of features in such end stage patients, hand made templates were created (FIG. 15) and used to form feature trend plots (FIG. 16 and 17). This figure shows seven templates developed on an a priori basis to study subject JM. Mask T (tumor) shown at the upper left was hand formed to coincide with the expected region of maximal abnormality. Mask D (surround) was chosen to represent a region of local spread. Mask MLQ (minus left anterior quadrant) covers the head everywhere except over the region of maximal abnormality. The four remaining masks covered the four quadrants of the head independently left anterior quadrant—LAQ, right anterior quadrant—RAQ, left posterior quadrant—LPQ, and right posterior quadrant—RPQ. This set of seven templates was then used to develop features and trend plates from all EEG and EP states for subject JM.

FIGS. 16 and 17 show nine graphs. Seven are feature trend plots (a, b, e, f, g, h, i) developed from the a priori templates shown in FIG. 15. The particular template or mask used to form each feature plotted is shown above the trend plot; the state during which the feature was created is shown to the left. Two graphs (c, d) pertain to behavioral variables showing the trend of right hand pegboard scores (PEGTR) and the correlation between EOP delta mask T and PEGTR.

EOP delta trend plots produced type C progressive change especially when formed from templates involving the left frontal region (see FIGS. 16, 17). As for the EOP delta max feature shown in FIG. 13, these features correlated highly with right handed behavioral variables. Note the peaks of feature value in FIG. 16a and 26b which are also noted in the behavioral variable PEGTR (FIG. 16c). There is an extremely high correlation of EOP delta mask T with PEGTR (FIG. 16d): r=0.86, T=5.57, p<0.001.

Other features more clearly defined a smooth type C response such as AER 120 mask T (FIG. 16e). Still others showed a change in progression midway about the 20 week mark, but seen for features BSE 120 mask D (FIG. 16f), VER 440 mask RAQ (FIG. 17g), and VER 440 mask MLQ (FIG. 17i).

As in the preceding analysis (based on first to control group templates), regions distant from the primary lesion were more likely to produce type A or B plots than were templates over the lesion. The best type A plots involved only the right anterior quadrant (VER 440, FIG. 17g), excluded the left anterior quadrant (VER 440, FIG. 17i), or surrounded the lesion (BSE 120, FIG. 16s).

Figure 19:
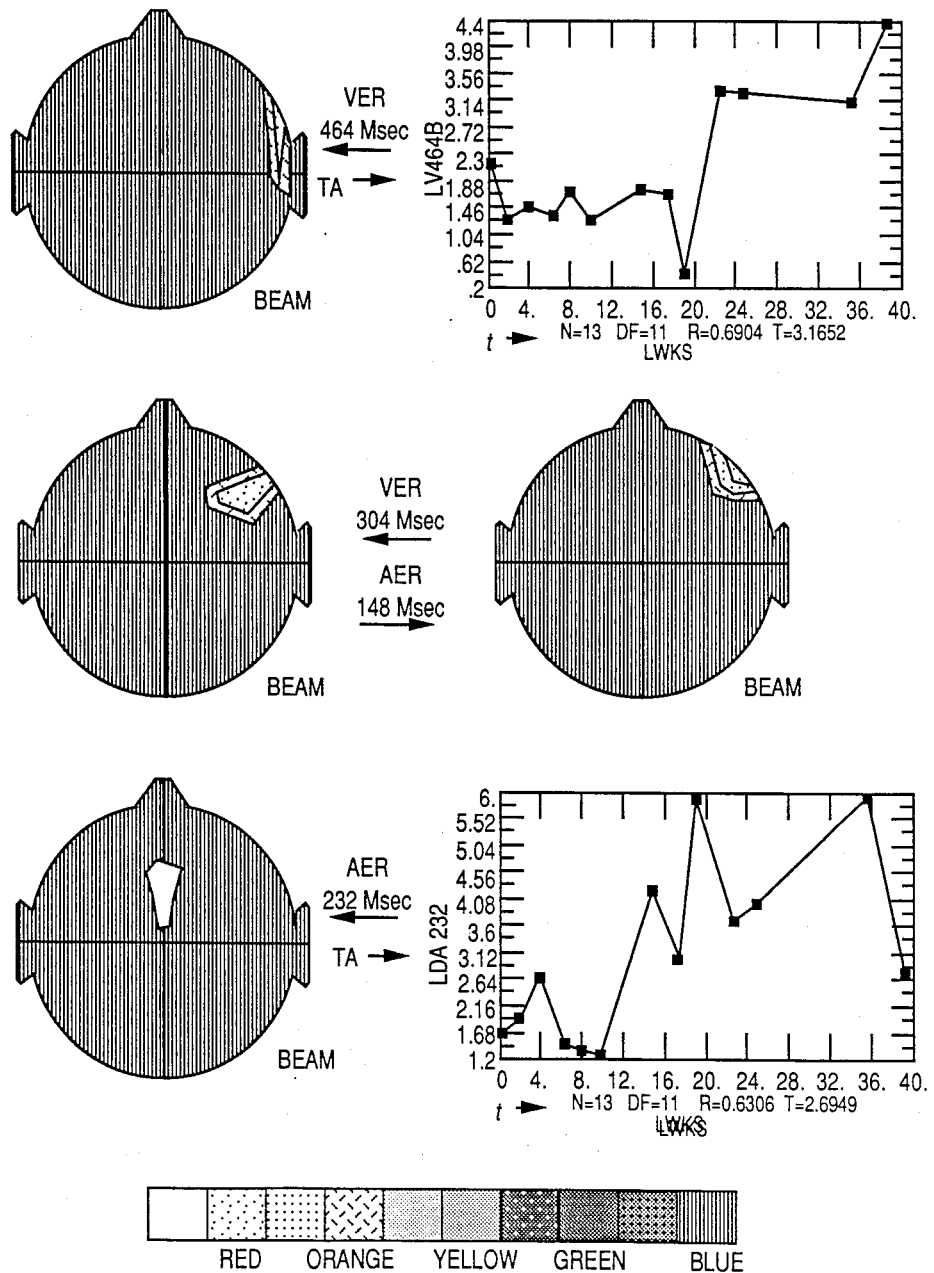

A retrospective analysis was undertaken comparing JM's first and last three studies, the results of which are summarized in FIGS. 18 and 19. FIG. 18 shows resulting templates closest to or over the maximum anatomical abnormality. Almost all produced type C plots, some of which were sensitive to the behavioral fluctuations at 8 and 20 weeks (e.g., EOP delta). FIG. 19 shows resulting templates distant from the maximal lesion. Some showed excellent type A trend plots (e.g., VER 464). It seems likely that the greater incidence of type A plots away from the lesion locus represents a combination of the contiguous spread and threshold phenomena, especially in late or end stage pathology.

FIGS. 18 and 19 show templates developed from t-SPM based on a two group comparison. The first group consisted of the first three studies, and the second group the final three studies of subject JM. The cutoff value for forming templates from t-SPM included the top 25% of t values above a t of 2.0. Resulting t-SPM and templates delineate regional change from the beginning to the end of the study period. In FIG. 18 regional change overlying the primary lesion is shown. Most features developed from such templates demonstrated trend plots similar to that shown for EOP delta (FIG. 18). In FIG. 19 regional change at a distance is shown with the typical trend plot for that group exemplified by VER 464 (FIG. 19). Note the relatively abrupt change at midpoint. A less clear midpoint change is seen for AER 232 (FIG. 19) which is at the edge of the original lesion.

Thus, it appears that templates overlying the lesion demonstrate type C trend plots and templates at a distance more type A or B trend plots.

FIGS. 20, 21 and 22 show examples of alternative methods for forming features and trend plots. FIGS. 20 and 21 exemplify the formation of templates from retrospective regression and correlational analyses. This method enables localization of regions showing maximal linear trends. Indeed the trend plots for EOP delta (FIG. 20) and EOP theta (FIG. 21) show higher correlations with time than their corresponding plots created from the prior first to control or first to last analyses. Once again this region of most significant linear trend is located distant from the primary lesion.

An alternative to the development of templates by t-SPM analysis is the use of regression or correlational analyses. In this process, data from each of the 20 electrodes are separately analyzed. The slope of the linear regression line is calculated for the data of each electrode across all studies and a single BEAM image made of the result of that analysis from all 20 electrodes. This is shown at the top left in FIG. 20 for EOP delta and to the top left of FIG. 21 for EOP theta. Similar images can be formed for the correlation coefficient (top right of both figures) and for the significance of the regression line (mid left of both figures). These images may be used to form templates as shown to the lower left of both figures for the slope significance. These in turn can produce features which can be used for trend plots (see lower right of both figures).

A disadvantage of this method is that it selects for a constant linear trend and in fact both resulting trend plots are type C. It is inherently a retrospective or exploratory technique. Other non-linear regression methods may prove of greater value in the delineation of type A and B responses.

FIG. 22A illustrates the processing technique of multivariate discriminant function analysis. A stepwise discriminant analysis was performed on three groups, JM's first, middle, and last studies. The first discriminant function plotted against time served to discriminate among the three groupings. However, the second discriminant function formed the best type C trend plot of the entire analysis. This process should be performed not only on one subject, but on all subjects as a group in an attempt to form a more generally useful discriminant function.

FIG. 22B represents an attempt to use spatially and temporally independent features in the formation of trend plots. Here the CCA feature (maximum cross correlation over all intervals for all electrodes) is formed from AER data and the resulting trend is plotted. Further work has suggested that CCA and spatial trajectory analysis (STA) features are particularly useful, especially when combined with discriminant function analysis.

In this figure we demonstrate additional methods for making features and form trend plots. The first is discriminant analysis. The goal is to develop a standardized discriminant score that will optimally display change over time. Here we illustrate the approach on just one subject, JM. This subject's first 5 sessions, last 5 sessions, and middle 3 sessions form the basis for a 3 group discriminant analysis. The best four features from a merit value comparison were used. From this 3 group comparison two discriminant functions are formed. The plot (FIG. 22A) of the first vs. time clearly discriminates among the three groupings, but shows no intuitively useful trend. However, the trend plot of the second discriminant function shows the best type C response produced for this subject.

The cross correlational analysis (CCA) and spatial-temporal analysis (STA) methods described in my co-pending applications filed on even date herewith may also be useful as generators of features for trend analysis. FIG. 22B shows a CCA feature developed from the AER (maximum cross correlation over all intervals for all electrodes). It shows a noisy type C response with the two discontinuities also noted in FIGS. 16a, 16b.

To summarize our findings are:

(1) Trend plots derived from neurophysiological features demonstrate progressive change in advance of clinical change for all subjects.

(2) Feature trend plots demonstrating abrupt worsening can be demonstrated for all subjects, however, in these same subjects other plots demonstrate continuous progression. Thus, some features appear sensitive to the low level continuous progression of the GBM while others parallel, but precede, more abrupt clinical change. For the latter a critical threshold effect is postulated.

(3) It is more difficult to demonstrate type A or B feature trend plots in patients with histories of multiple recurrences and remissions.

(4) Motor indices correlate well with neurophysiological features only late in a period of remission or in patients with histories of multiple recurrence.

(5) Neurophysiological progression manifests itself not only by increased abnormality overlying the original lesion, but by contiguous spread to adjacent regions. A correlate of this is finding that recurrence appears to be associated with regional electrophysiological change nearby, but not necessarily overlying, the original process.

(6) We postulate a "saturation effect" where the brain no longer produces increasing electrical abnormality with progression of the underlying lesion.

(7) EEG derived feature types seem to show more spatially restricted abnormalities than EP types.

(8) There is a complex relation between feature type, spatial proximity to the tumor, and resulting trend plot morphology. This appears to derive from an involved interaction between saturation, contiguous spread, degree of original pathology, and feature type. A correlate of this is that predictive trend plots may best be found near, but not over early/small lesions with EEG type features and may best be found at a distance from late/large lesions with EP type features.

(9) The STA and CCA feature generation process shows promise for generating useful trend plots while feature combination (STA, CCA, T-SPM) via a discriminant function may provide a more universally applicable predictive process.

The trend analysis method has been adapted to follow patients at risk for recurrent GBM, to the problem of tracking patients over short periods of time following the administration of intravenous drugs. Our topographic trend analysis (TTA) method has augmented the classical "pentathol activation" procedure originally developed by Lombroso and Erba to better classify epileptics. Our findings surprisingly demonstrate that I.V. pentathol induces clinically useful regional changes in EEG slow activity as well as fast activity. Furthermore, fast activity may be increased as well as decreased over lesions, especially those that are electrically irritable.

Other embodiments of the invention are within the following claims.

What is claimed is:

1. A method of detecting a change in brain electrical activity, comprising the steps of:
choosing a template defining a selected region of a patient's brain electrical activity map,
summing the values of the brain electrical activity map within the area defined by said template to form a feature,
plotting said feature versus time to form a trend plot, detecting a change in said trend plot characteristic of said change in brain electrical activity.

2. The method of claim 1 wherein the change being detected is indicative of the growth of a lesion.

3. The method of claim 2 wherein said step of choosing comprises selecting a plurality of concentric, ring-shaped templates which surround the area of said brain electrical activity map corresponding to said lesion, and wherein trend plots for each template are prepared.

4. The method of claim 2 wherein said step of choosing comprises selecting a template in the shape of a ring surrounding the area of the brain electrical activity map corresponding to said lesion.

5. The method of claim 4 wherein the difference between the inner and outer radius of said ring is between ¼ and ¾ the diameter of the abnormality if reduced to roughly circular size.

6. The method of claim 4 wherein said step of plotting comprises plotting trend plots for at least two templates, one corresponding to the area of the lesion and another to a ring surrounding the lesion, so that it can be determined whether the lesion is growing in the same area or expanding outside that area.

7. The method of claim 1 wherein said step of choosing comprises choosing a template in the area of the brain electrical activity map that relates to a suspected location of a lesion.

8. The method of claim 1 wherein said step of choosing comprises determining the location of one or more portions of said brain electrical activity map that varies from a predetermined normal brain electrical activity map and choosing the location of said template based on the location of said one or more portions.

9. The method of claim 8 wherein a t-statistic statistical probability map is prepared to establish the location of said one or more portions.

10. The method of claim 8 wherein a procedure for establishing the location of said one or more portions utilizes one of the following: slope of regression line, significance of regression line, or correlation coefficient.

11. The method of claim 8 wherein said template is a ring surrounding one of said one or more portions.

12. The method of claim 11 wherein the difference between the inner and outer radius of said ring is between ¼ and ¾ the diameter of the abnormality if reduced to roughly circular size.

13. The method of claim 1 wherein said detected change in the trend plot is a change in slope.

14. The method of claim 1 wherein said detected change in the trend plot is exceeding a predetermined threshold.

15. The method of claim 1 wherein a brain electrical activity map derived from EEG data is used to determine said feature.

16. The method of claim 1 wherein a brain electrical activity map derived from EP data is used to determine said feature.

17. The method of claim 1 wherein said step of choosing comprises selecting a plurality of concentric ring-shaped templates, and wherein trend plots for each template are prepared.

18. The method of claim 1 wherein said template is chosen to correspond to one of the quadrants of the head or to known anatomical boundaries.

19. The method of claim 1 wherein said step of choosing comprises studying a patient's brain electrical activity maps over a period of time to determine the location of portions of said maps that are changing over time, and selecting the template based on the location of said portions.

* * * * *

UNITED STATES PATENT AND TRADEMARK OFFICE
CERTIFICATE OF CORRECTION

PATENT NO. : 4,815,474

DATED : March 28, 1989

INVENTOR(S) : Frank H. Duffy

It is certified that error appears in the above-identified patent and that said Letters Patent is hereby corrected as shown below:

On the title page,
Under References Cited:

4,254,779 Miyata et al., the Class/Subclass should be --364/717 XR--.

Other Publications:

The following reference should be included:

--Salf, J. et al. "uP-based System for On-line Analysis and Display of Brain Electric Activity," International Appln. (PCT) Publ. No. WO 83/03745 Publ. Date Nov. 10, 1983 (Copy 128/731)--.

In the Specification:

Col. 2, line 23, insert --is-- after "one".

Signed and Sealed this

Seventeenth Day of April, 1990

Attest:

HARRY F. MANBECK, JR.

*Attesting Officer*          *Commissioner of Patents and Trademarks*